US007235386B2

(12) United States Patent
Padgett et al.

(10) Patent No.: US 7,235,386 B2
(45) Date of Patent: *Jun. 26, 2007

(54) METHOD OF INCREASING COMPLEMENTARITY IN A HETERODUPLEX

(75) Inventors: Hal S. Padgett, Vacaville, CA (US); John A. Lindbo, Vacaville, CA (US); Wayne P. Fitzmaurice, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 70 days.

This patent is subject to a terminal disclaimer.

(21) Appl. No.: 10/205,772

(22) Filed: Jul. 25, 2002

(65) Prior Publication Data

US 2003/0186261 A1    Oct. 2, 2003

Related U.S. Application Data

(62) Division of application No. 10/066,390, filed on Feb. 1, 2002.

(60) Provisional application No. 60/268,785, filed on Feb. 14, 2001, provisional application No. 60/266,386, filed on Feb. 2, 2001.

(51) Int. Cl.
*C12P 19/34* (2006.01)
*C12Q 1/68* (2006.01)
*C07H 21/02* (2006.01)
*C07H 21/04* (2006.01)
*C07H 21/00* (2006.01)

(52) U.S. Cl. ............... 435/91.2; 435/6; 435/91.1; 536/23.1; 536/24.3; 536/24.33; 536/25.3

(58) Field of Classification Search ............ 435/6, 435/91.1, 91.2, 91.51, 183; 436/94; 536/23.1, 536/24.3, 24.33, 25.3
See application file for complete search history.

(56) References Cited

U.S. PATENT DOCUMENTS

| 4,994,368 | A | 2/1991 | Goodman et al. | |
| 5,459,039 | A | 10/1995 | Modrich et al. | 435/6 |
| 5,556,747 | A | 9/1996 | Kumar | |
| 5,679,522 | A | 10/1997 | Modrich et al. | |
| 5,683,877 | A | 11/1997 | Lu-Chang et al. | 435/6 |
| 5,723,323 | A | 3/1998 | Kauffman et al. | |
| 5,795,747 | A | 8/1998 | Henco et al. | 435/91.1 |
| 5,861,482 | A | 1/1999 | Modrich et al. | |
| 5,869,245 | A | 2/1999 | Yeung | |
| 5,922,539 | A | 7/1999 | Modrich et al. | |
| 6,057,103 | A | 5/2000 | Short | 435/6 |
| 6,165,793 | A | 12/2000 | Stemmer | 435/440 |
| 6,391,557 | B1 | 5/2002 | Yeung | |
| 6,537,746 | B2* | 3/2003 | Arnold et al. | 435/6 |
| 6,783,941 | B2* | 8/2004 | Vind | 435/6 |
| 6,846,655 | B1 | 1/2005 | Wagner et al. | |
| 7,056,740 | B2* | 6/2006 | Padgett et al. | 435/440 |
| 2002/0045175 | A1 | 4/2002 | Wang et al. | |
| 2003/0017477 | A1 | 1/2003 | Vind | |
| 2004/0048268 | A1 | 3/2004 | Delcourt et al. | |

FOREIGN PATENT DOCUMENTS

| DE | 4112440 | 10/1992 |
| DE | 19953854 | 5/2001 |
| FR | 2789696 | 8/2000 |
| WO | WO 92/18645 | 10/1992 |
| WO | WO 93/20233 | 10/1993 |
| WO | WO 96/40902 | 12/1996 |
| WO | WO 97/37011 | 10/1997 |
| WO | WO 97/46701 | 12/1997 |
| WO | WO 99/28451 | 6/1999 |
| WO | WO 99/29902 | 6/1999 |
| WO | WO 00/71730 | 11/2000 |
| WO | WO 01/34835 | 5/2001 |
| WO | WO 01/62974 | 8/2001 |
| WO | WO 02/24953 | 3/2002 |
| WO | WO 02/079468 | 10/2002 |
| WO | WO 04/035771 | 4/2004 |

OTHER PUBLICATIONS attachment for Taq DNA polymerase.*
Biswas and Hsieh, "Identification and characterization of a thermostable MutS homolog from *Thermus aquaticus*", *J. Biol. Chem.* (1996) 271(9):5040-5048.
Kraemer and Digiovanna, "Topical enzyme therapy for skin diseases?", *J. Am. Acad. Dermatol.* (2002) 46:463-6.
O'Grady, et al., "DNA repair in thermophiles: investigation of DNA-binding activities in *Thermus aquaticus*", *Biochem. Soc. Tranactions* (1997) 25:319-22.

(Continued)

*Primary Examiner*—Frank Lu
(74) *Attorney, Agent, or Firm*—Wayne P. Fitzmaurice; R. Thomas Gallegos; John E. Tarcza

(57) ABSTRACT

We describe here an in vitro method of increasing complementarity in a heteroduplex polynucleotide sequence. The method uses annealing of opposite strands to form a polynucleotide duplex with mismatches. The heteroduplex polynucleotide is combined with an effective amount of enzymes having strand cleavage activity, 3' to 5' exonuclease activity, and polymerase activity, and allowing sufficient time for the percentage of complementarity to be increased within the heteroduplex. Not all heteroduplex polynucleotides will necessarily have all mismatches resolved to complementarity. The resulting polynucleotide is optionally ligated. Several variant polynucleotides result. At sites where either of the opposite strands has templated recoding in the other strand, the resulting percent complementarity of the heteroduplex polynucleotide sequence is increased. The parent polynucleotides need not be cleaved into fragments prior to annealing heterologous strands. Therefore, no reassembly is required.

7 Claims, 2 Drawing Sheets

OTHER PUBLICATIONS

Sugahara, et al., "Crystal structure of repair enzyme of oxidatively damaged DNA, MutM (Fpg), from an extreme thermophile, *Thermus thermophilus* HB8", *EMBO J* (2000) 19(15):3857-3869.

Wang, "Creating hybrid genes by homologous recombination", *Disease Markers* (2000) 16:3-13.

Birkenkamp and Kemper, "In vitro processing of heteroduplex loops and mismatches by Endonuclease VII", *DNA Research*, 1995, vol. 2, pp. 9-14.

Abastado, et al., "Processing of complex heteroduplexes in *Escherichia coli* and *Cos*-1 monkey cells", *Proc. Natl. Acad. Sci. USA*, Sep. 1984, vol. 81, pp. 5792-5796.

Cami, et al., "Correction of complex heteroduplexes made of mouse H-2 gene sequences in *Escherichia coli* K-12", *Proc. natl. Acad. Sci. USA,* Jan. 1984, vol. 81, pp. 503-507.

Chang, et al., "Recombination following transformation of *Escherichia coli* by heteroduplex plasmid DNA molecules", *Gene*, 1984, vol. 29, pp. 255-264, Elsevier.

Cotton, "Slowly but surely towards better scanning for mutations", *TIG*, Feb. 1997, vol. 13, No. 2, pp. 43-46, Elsevier Science Ltd.

Joyce, "Directed Molecular Evolution", *Scientific American,* Dec. 1992, pp. 90-97.

Kulinski, et al., "CEL I Enzymatic Mutation Detection Assay", *Biotechniques*, Jul. 2000, vol. 29, pp. 44-48.

Lahue, et al., "Requirement for d(GATC) sequences in *Escherichia coli mutHLS* mismatch correction", *Proc. Natl. Acad. Sci. USA*, Mar. 1987, vol. 84, pp. 1482-1486.

Modrich, "Strand-specific Mismatch Repair in Mammalian Cells", *The Journal of Biological Chemistry,* Oct. 3, 1997, vol. 272, No. 4, pp. 24727-24730, The American Society of for Biochemistry and Molecular Biology, Inc., Bethesda, MD.

Oleykowksi, et al., "Mutation detection using a novel plant endonuclease", *Nucleic Acids Research,* 1998, vol. 26, No. 20, pp. 4597-4602, Oxford University Press, United Kingdom.

Oleykowski, et al., "Incision at Nucleotide Insertions/Deletions and Base Pair Mismatches by the SP Nuclease of Spinach", *Biochemistry,* 1999, vol. 38, pp. 2200-2205, American Chemical Society, Columbus, OH.

Robertson, "Directed evolution patent could have major impact", *Nature Biotechnology,* May 1998, vol. 16, p. 411.

Solaro, et al., "Endonuclease VII of Phage T4 Triggers Mismatch Correction in Vitro", *J. Mol. Biol.,* 1993, vol. 230, pp. 868-877, Academic Press Limited.

Volkov, et al., "Random Chimeragenesis by Heteroduplex Recombination", *Methods in Enzymology,* 2000, vol. 328, pp. 456-463, Academic Press.

Volkov, et al., "Recombination and chimeragenesis by in vitro heteroduplex formation and in vivo repair", *Nucleic Acids Research,* 1999, vol. 27, No. 18, pp. e18 (i-vi), Oxford University Press.

Yang, et al., "Purification, Cloning, and Characterization of the CEL I Nuclease", *Biochemistry,* 2000, vol. 39, pp. 3533-3541, American Chemical Society.

* cited by examiner

```
                                                              5'-AGACCGATCGATTG-3'   SEQ ID NO:20
5'-AGATCGATCAATTG-3'   SEQ ID NO:18                              ||||||||||||
A.  ||||||||||||                                          B.
    3'-TCTAGCTAGTTAAC-5'   SEQ ID NO:19                         3'-TCTGGCTAGCTAAC-5'  SEQ ID NO:21

5'-AGATCGATCAATTG-3'   SEQ ID NO:18
         HETERODUPLEX    |||    ||||  |||
                        3'-TCTGGCTAGCTAAC-5'   SEQ ID NO:21

5'-AGATCGATCGATTG-3'   SEQ ID NO:18                              5'-AGACCGATCGATTG-3'   SEQ ID NO:20
A.  ||||||||||||                                          B.        ||||||||||||
    3'-TCTAGCTAGTTAAC-5'   SEQ ID NO:19                            3'-TCTGGCTAGCTAAC-5'  SEQ ID NO:21

5'-AGATCGATCAATTG-3'   SEQ ID NO:22                              5'-AGACCGATCAATTG-3'   SEQ ID NO:24
X.  ||||||||||||                                          Y.        ||||||||||||
    3'-TCTAGCTAGTTAAC-5'   SEQ ID NO:23                            3'-TCTGGCTAGTTAAC-5'  SEQ ID NO:25
```

X
5'-AGATCAATTG-3'  1+
   ||||||||||
3'-TCTAGTTAAC-5'  2-

* *

Y
5'-AGACCGATTG-3'  3+
   ||||||||||
3'-TCTGGCTAAC-5'  4-

FIG. 2B

| POSSIBLE STRAND COMBINATIONS | POSSIBLE +/- STRAND COMBINATIONS | PARTIALLY COMPLEMENTARY POPULATIONS |
|---|---|---|
| 1+/2- | √ | |
| 1+/3+ | | |
| 1+/4- | √ | √ |
| 2-/3+ | √ | √ |
| 2-/4- | | |
| 3+/4- | √ | |

METHOD OF INCREASING COMPLEMENTARITY IN A HETERODUPLEX

This application is a divisional application of U.S. patent application Ser. No. 10/066,390 filed Feb. 1, 2002, which claims benefit to U.S. Provisional Application No. 60/266,386, filed Feb. 2, 2001, and of U.S. Provisional Application No. 60/268,785, Filed Feb. 14, 2001, and are both incorporated herein by reference.

BACKGROUND OF THE INVENTION

1. Field of the Invention

The invention relates generally to molecular biology and more specifically to methods of generating populations of related nucleic acid molecules.

2. Background Information

DNA shuffling is a powerful tool for obtaining recombinants between two or more DNA sequences to evolve them in an accelerated manner. The parental, or input, DNAs for the process of DNA shuffling are typically mutants or variants of a given gene that have some improved character over the wild-type. The products of DNA shuffling represent a pool of essentially random reassortments of gene sequences from the parental DNAs that can then be analyzed for additive or synergistic effects resulting from new sequence combinations.

Recursive sequence reassortment is analogous to an evolutionary process where only variants with suitable properties are allowed to contribute their genetic material to the production of the next generation. Optimized variants are generated through DNA shuffling-mediated sequence reassortment followed by testing for incremental improvements in performance. Additional cycles of reassortment and testing lead to the generation of genes that contain new combinations of the genetic improvements identified in previous rounds of the process. Reassorting and combining beneficial genetic changes allows an optimized sequence to arise without having to individually generate and screen all possible sequence combinations.

This differs sharply from random mutagenesis, where subsequent improvements to an already improved sequence result largely from serendipity. For example, in order to obtain a protein that has a desired set of enhanced properties, it may be necessary to identify a mutant that contains a combination of various beneficial mutations. If no process is available for combining these beneficial genetic changes, further random mutagenesis will be required. However, random mutagenesis requires repeated cycles of generating and screening large numbers of mutants, resulting in a process that is tedious and highly labor intensive. Moreover, the rate at which sequences incur mutations with undesirable effects increases with the information content of a sequence. Hence, as the information content, library size, and mutagenesis rate increase, the ratio of deleterious mutations to beneficial mutations will increase, increasingly masking the selection of further improvements. Lastly, some computer simulations have suggested that point mutagenesis alone may often be too gradual to allow the large-scale block changes that are required for continued and dramatic sequence evolution.

There are a number of different techniques used for random mutagenesis. For example, one method utilizes error-prone polymerase chain reaction (PCR) for creating mutant genes in a library format, (Cadwell and Joyce, 1992; Gram et al., 1992). Another method is cassette mutagenesis (Arkin and Youvan, 1992; Delagrave et al., 1993; Delagrave and Youvan, 1993; Goldman and Youvan, 1992; Hermes et al., 1990; Oliphant et al., 1986; Stemmer et al., 1993) in which the specific region to be optimized is replaced with a synthetically mutagenized oligonucleotide.

Error-prone PCR uses low-fidelity polymerization conditions to introduce a low level of point mutations randomly over a sequence. A limitation to this method, however, is that published error-prone PCR protocols suffer from a low processivity of the polymerase, making this approach inefficient at producing random mutagenesis in an average-sized gene.

In oligonucleotide-directed random mutagenesis, a short sequence is replaced with a synthetically mutagenized oligonucleotide. To generate combinations of distant mutations, different sites must be addressed simultaneously by different oligonucleotides. The limited library size that is obtained in this way, relative to the library size required to saturate all sites, means that many rounds of selection are required for optimization. Mutagenesis with synthetic oligonucleotides requires sequencing of individual clones after each selection round followed by grouping them into families, arbitrarily choosing a single family, and reducing it to a consensus motif. Such a motif is resynthesized and reinserted into a single gene followed by additional selection. This step creates a statistical bottleneck, is labor intensive, and is not practical for many rounds of mutagenesis.

For these reasons, error-prone PCR and oligonucleotide-directed mutagenesis can be used for mutagenesis protocols that require relatively few cycles of sequence alteration, such as for sequence fine-tuning, but are limited in their usefulness for procedures requiring numerous mutagenesis and selection cycles, especially on large gene sequences.

As discussed above, prior methods for producing improved gene products from randomly mutated genes are of limited utility. One recognized method for producing a wide variety of randomly reasserted gene sequences uses enzymes to cleave a long nucleotide chain into shorter pieces. The cleaving agents are then separated from the genetic material, and the material is amplified in such a manner that the genetic material is allowed to reassemble as chains of polynucleotides, where their reassembly is either random or according to a specific order. ((Stemmer, 1994a; Stemmer, 1994b), U.S. Pat. No. 5,605,793, U.S. Pat. No. 5,811,238, U.S. Pat. No. 5,830,721, U.S. Pat. No. 5,928,905, U.S. Pat. No. 6,096,548, U.S. Pat. No. 6,117,679, U.S. Pat. No. 6,165,793, U.S. Pat. No. 6,153,410). A variation of this method uses primers and limited polymerase extensions to generate the fragments prior to reassembly (U.S. Pat. No. 5,965,408, U.S. Pat. No. 6,159,687).

However, both methods have limitations. These methods suffer from being technically complex. This limits the applicability of these methods to facilities that have sufficiently experienced staffs. In addition there are complications that arise from the reassembly of molecules from fragments, including unintended mutagenesis and the increasing difficulty of the reassembly of large target molecules of increasing size, which limits the utility of these methods for reassembling long polynucleotide strands.

Another limitation of these methods of fragmentation and reassembly-based gene shuffling is encountered when the parental template polynucleotides are increasingly heterogeneous. In the annealing step of those processes, the small polynucleotide fragments depend upon stabilizing forces that result from base-pairing interactions to anneal properly. As the small regions of annealing have limited stabilizing forces due to their short length, annealing of highly complementary sequences is favored over more divergent sequences. In such instances these methods have a strong tendency to regenerate the parental template polynucleotides due to annealing of complementary single-strands from a particular parental template. Therefore, the parental templates essentially reassemble themselves creating a background of unchanged polynucleotides in the library that increases the difficulty of detecting recombinant molecules. This problem becomes increasingly severe as the parental templates become more heterogeneous, that is, as the percentage of sequence identity between the parental templates decreases. This outcome was demonstrated by Kikuchi, et al., (Gene 243:133-137, 2000) who attempted to generate recombinants between xylE and nahH using the methods of family shuffling reported by Patten et al., 1997; Crameri et al., 1998; Harayama, 1998; Kumamaru et al., 1998; Chang et al., 1999; Hansson et al., 1999). Kikuchi, et al., found that essentially no recombinants (<1%) were generated. They also disclosed a method to improve the formation of chimeric genes by fragmentation and reassembly of single-stranded DNAs. Using this method, they obtained chimeric genes at a rate of 14 percent, with the other 86 percent being parental sequences.

The characteristic of low-efficiency recovery of recombinants limits the utility of these methods for generating novel polynucleotides from parental templates with a lower percentage of sequence identity, that is, parental templates that are more diverse. Accordingly, there is a need for a method of generating gene sequences that addresses these needs.

The present invention provides a method that satisfies the aforementioned needs, and also provides related advantages as well.

SUMMARY OF THE INVENTION

The present invention provides a method for reasserting mutations among related polynucleotides, in vitro, by forming heteroduplex molecules and then addressing the mismatches such that sequence information at sites of mismatch is transferred from one strand to the other. In one preferred embodiment, the mismatches are addressed by incubating the heteroduplex molecules in a reaction containing a mismatch nicking enzyme, a polymerase with a 3' to 5' proofreading activity in the presence of dNTPs, and a ligase. These respective activities act in concert such that, at a given site of mismatch, the heteroduplex is nicked, unpaired bases are excised then replaced using the opposite strand as a template, and nicks are sealed. Output polynucleotides are amplified before cloning, or cloned directly and tested for improved properties. Additional cycles of mismatch resolution reassortment and testing lead to further improvement.

BRIEF DESCRIPTION OF THE FIGURES

FIG. 1 depicts the process of Genetic ReAssortment by Mismatch Resolution (GRAMMR). Reassortment is contemplated between two hypothetical polynucleotides differing at at least two nucleotide positions. Annealing between the top strand of A (SEQ ID NO:18; 5'-AGATCGAT-CAATTG-3') and the bottom strand of B (fully complementary strand of SEQ ID NO:19; SEQ ID NO:19 is 5'-AGAC-CGATCGATTG-3') is shown (labeled HETERODUPLEX) which results in mismatches at the two positions. After the process of reassortment by mismatch resolution, four distinct product polynucleotides are seen, the parental types A (SEQ ID NO:18 and its fully complementary strand) and B (SEQ ID NO:19 and its fully complementary strand), and the reassorted products C (SEQ ID NO:20; 5'-AGATCGATC-GATTG-3' and its fully complementary strand) and D (SEQ ID NO: 21; 5'-AGACCGATCAATTG-3' and its fully complementary strand).

FIG. 2 depicts an exemplary partially complementary nucleic acid population of two molecules. FIG. 2A shows the sequence of two nucleic acid molecules "X" (SEQ ID NO:16; 5'-AGATCAATTG-3' and its fully complementary strand) and "Y" (SEQ ID NO:17; 5'-AGACCGATTG-3' and its fully complementary strand) having completely complementary top/bottom strands 1+/2− and 3+/4−, respectively. The positions of differing nucleotides between the nucleic acids X and Y are indicated (*). FIG. 2B shows possible combinations of single strands derived from nucleic acids X and Y after denaturing and annealing and indicates which of those combinations would comprise a partially complementary nucleic acid population of two.

DEFINITIONS

As used herein the term "amplification" refers to a process where the number of copies of a polynucleotide is increased.

As used herein, "annealing" refers to the formation of at least partially double stranded nucleic acid by hybridization of at least partially complementary nucleotide sequences. A partially double stranded nucleic acid can be due to the hybridization of a smaller nucleic acid strand to a longer nucleic acid strand, where the smaller nucleic acid is 100% identical to a portion of the larger nucleic acid. A partially double stranded nucleic acid can also be due to the hybridization of two nucleic acid strands that do not share 100% identity but have sufficient homology to hybridize under a particular set of hybridization conditions.

As used herein, "clamp" refers to a unique nucleotide sequence added to one end of a polynucleotide, such as by incorporation of the clamp sequence into a PCR primer. The clamp sequences are intended to allow amplification only of polynucleotides that arise from hybridization of strands from different parents (i.e., heteroduplex molecules) thereby ensuring the production of full-length hybrid products as described previously (Skarfstad, J. Bact, vol 182, No 11, P. 3008-3016).

As used herein the term "cleaving" means digesting the polynucleotide with enzymes or otherwise breaking phosphodiester bonds within the polynucleotide.

As used herein the term "complementary basepair" refers to the correspondence of DNA (or RNA) bases in the double helix such that adenine in one strand is opposite thymine (or uracil) in the other strand and cytosine in one strand is opposite guanine in the other.

As used herein the term "complementary to" is used herein to mean that the complementary sequence is identical to the reverse-complement of all or a portion of a reference polynucleotide sequence or that each nucleotide in one strand is able to form a base-pair with a nucleotide, or analog thereof in the opposite strand. For illustration, the nucleotide sequence "TATAC" is complementary to a reference sequence "GTATA".

As used herein, "denaturing" or "denatured," when used in reference to nucleic acids, refers to the conversion of a double stranded nucleic acid to a single stranded nucleic acid. Methods of denaturing double stranded nucleic acids are well known to those skilled in the art, and include, for example, addition of agents that destabilize base-pairing, increasing temperature, decreasing salt, or combinations thereof. These factors are applied according to the complementarity of the strands, that is, whether the strands are 100% complementary or have one or more non-complementary nucleotides.

As used herein the term "desired functional property" means a phenotypic property, which include but are not limited to, encoding a polypeptide, promoting transcription of linked polynucleotides, binding a protein, improving the function of a viral vector, and the like, which can be selected or screened for. Polynucleotides with such desired functional properties, can be used in a number of ways, which include but are not limted to expression from a suitable plant, animal, fungal, yeast, or bacterial expression vector, integration to form a transgenic plant, animal or microorganism, expression of a ribozyme, and the like.

As used herein the term "DNA shuffling" is used herein to indicate recombination between substantially homologous but non-identical sequences.

As used herein, the term "effective amount" refers to the amount of an agent necessary for the agent to provide its desired activity. For the present invention, this determination is well within the knowledge of those of ordinary skill in the art.

As used herein the term "exonuclease" refers to an enzyme that cleaves nucleotides one at a time from an end of a polynucleotide chain, that is, an enzyme that hydrolyzes phosphodiester bonds from either the 3' or 5' terminus of a polynucleotide molecule. Such exonucleases, include but are not limited to T4 DNA polymerase, T7 DNA polymerase, E. coli Pol 1, and Pfu DNA polymerase. The term "exonuclease activity" refers to the activity associated with an exonuclease. An exonuclease that hydrolyzes in a 3' to 5' direction is said to have "3' to 5' exonuclease activity." Similarly an exonuclease with 5' to 3' activity is said to have "5' to 3' exonuclease activity." It is noted that some exonucleases are known to have both 3' to 5', 5' to 3' activity, such as, E. coli Pol I.

As used herein, "Genetic Reassortment by Mismatch Resolution (GRAMMR)" refers to a method for reasserting sequence variations among related polynucleotides by forming heteroduplex molecules and then addressing the mismatches such that information is transferred from one strand to the other.

As used herein, "granularity" refers to the amount of a nucleic acid's sequence information that is transferred as a contiguous sequence from a template polynucleotide strand to a second polynucleotide strand. As used herein, "template sequence" refers to a first single stranded polynucleotide sequence that is partially complementary to a second polynucleotide sequence such that treatment by GRAMMR results in transfer of genetic information from the template strand to the second strand.

The larger the units of sequence information transferred from a template strand, the higher the granularity. The smaller the blocks of sequence information transferred from the template strand, the lower or finer the granularity. Lower granularity indicates that a DNA shuffling or reassortment method is able to transfer smaller discrete blocks of genetic information from the template strand to the second strand. The advantage of a DNA shuffling or reassortment method with lower granularity is that it is able to resolve smaller nucleic acid sequences from others, and to transfer the sequence information. DNA shuffling or reassortment methods that return primarily high granularity are not readily able to resolve smaller nucleic acid sequences from others.

As used herein the term "heteroduplex polynucleotide" refers to a double helix polynucleotide formed by annealing single strands, typically separate strands, where the strands are non-identical. A heteroduplex polynucleotide may have unpaired regions existing as single strand loops-or bubbles. A heteroduplex polynucleotide region can also be formed by one single-strand polynucleotide wherein partial self-complementarity allows the formation of a stem-loop structure where the annealing portion of the strand is non-identical.

As used herein the term "heteroduplex DNA" refers to a DNA double helix formed by annealing single strands, typically separate strands), where the strands are non-identical. A heteroduplex DNA may have unpaired regions existing as single strand loops or bubbles. A heteroduplex DNA region can also be formed by one single-strand polynucleotide wherein partial self-complementarity allows the formation of a stem-loop structure where the annealing portion of the strand is non-identical.

As used herein the term "homologous" means that one single-stranded nucleic acid sequence may hybridize to an at least partially complementary single-stranded nucleic acid sequence. The degree of hybridization may depend on a number of factors including the amount of identity between the sequences and the hybridization conditions such as temperature and salt concentrations as discussed later.

Nucleic acids are "homologous" when they are derived, naturally or artificially, from a common ancestor sequence. During natural evolution, this occurs when two or more descendent sequences diverge from a parent sequence over time, i.e., due to mutation and natural selection. Under artificial conditions, divergence occurs, e.g., in one of two basic ways. First, a given sequence can be artificially recombined with another sequence, as occurs, e.g., during typical cloning, to produce a descendent nucleic acid, or a given sequence can be chemically modified, or otherwise manipulated to modify the resulting molecule. Alternatively, a nucleic acid can be synthesized de novo, by synthesizing a nucleic acid that varies in sequence from a selected parental nucleic acid sequence. When there is no explicit knowledge about the ancestry of two nucleic acids, homology is typically inferred by sequence comparison between two sequences. Where two nucleic acid sequences show sequence similarity over a significant portion of each of the nucleic acids, it is inferred that the two nucleic acids share a common ancestor. The precise level of sequence similarity that establishes homology varies in the art depending on a variety of factors.

For purposes of this disclosure, two nucleic acids are considered homologous where they share sufficient sequence identity to allow GRAMMR-mediated information transfer to occur between the two nucleic acid molecules.

As used herein the term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide.

As used herein the term "increase in percent complementarity" means that the percentage of complementary base-pairs in a heteroduplex molecule is made larger.

As used herein the term, "ligase" refers to an enzyme that rejoins a broken phosphodiester bond in a nucleic acid.

As used herein the term "mismatch" refers to a base-pair that is unable to form normal base-pairing interactions (i.e., other than "A" with "T" (or "U"), or "G" with "C").

As used herein the term "mismatch resolution" refers to the conversion of a mismatched base-pair into a complementary base-pair.

As used herein the term "mutations" means changes in the sequence of a wild-type or reference nucleic acid sequence or changes in the sequence of a polypeptide. Such mutations can be point mutations such as transitions or transversions. The mutations can be deletions, insertions or duplications.

As used herein the term "nick translation" refers to the property of a polymerase where the combination of a 5'-to-3' exonuclease activity with a 5'-to-3' polymerase activity allows the location of a single-strand break in a double-stranded polynucleotide (a "nick") to move in the 5'-to-3' direction.

As used herein, the term "nucleic acid" or "nucleic acid molecule" means a polynucleotide such as deoxyribonucleic acid (DNA) or ribonucleic acid (RNA) and encompasses single-stranded and double-stranded nucleic acid as well as an oligonucleotide. Nucleic acids useful in the invention include genomic DNA, cDNA, mRNA and synthetic oligonucleotides, and can represent the sense strand, the antisense strand, or both. A nucleic acid generally incorporates the four naturally occurring nucleotides adenine, guanine, cytosine, and thymidine/uridine. An invention nucleic acid can also incorporate other naturally occurring or non-naturally occurring nucleotides, including derivatives thereof, so long as the nucleotide derivatives can be incorporated into a polynucleotide by a polymerase at an efficiency sufficient to generate a desired polynucleotide product.

As used herein, a "parental nucleic acid" refers to a double stranded nucleic acid having a sequence that is 100% identical to an original single stranded nucleic acid in a starting population of partially complementary nucleic acids. Parental nucleic acids would include, for example in the illustration of FIG. 2, nucleic acids X and Y if partially complementary nucleic acid combinations 1+/4− or 2−/3+ were used as a starting population in an invention method.

As used herein, "partially complementary" refers to a nucleic acid having a substantially complementary sequence to another nucleic acid but that differs from the other nucleic acid by at least two or more nucleotides. As used herein, "partially complementary nucleic acid population" refers to a population of nucleic acids comprising nucleic acids having substantially complementary sequences but no nucleic acids having an exact complementary sequence for any other member of the population. As used herein, any member of a partially complementary nucleic acid population differs from another nucleic acid of the population, or the complement thereto, by two or more nucleotides. As such, a partially complementary nucleic acid specifically excludes a population containing sequences that are exactly complementary, that is, a complementary sequence that has 100% complementarity. Therefore, each member of such a partially complementary nucleic acid population differs from other members of the population by two or more nucleotides, including both strands. One strand is designated the top strand, and its complement is designated the bottom strand. As used herein, "top" strand refers to a polynucleotide read in the 5' to 3' direction and the "bottom" its complement. It is understood that, while a sequence is referred to as bottom or top strand, such a designation is intended to distinguish complementary strands since, in solution, there is no orientation that fixes a strand as a top or bottom strand.

For example, a population containing two nucleic acid members can be derived from two double stranded nucleic acids, with a potential of using any of the four strands to generate a single stranded partially complementary nucleic acid population. An example of potential combinations of strands of two nucleic acids that can be used to obtain a partially complementary nucleic acid population of the invention is shown in FIG. 2. The two nucleic acid sequences that are potential members of a partially complementary nucleic acid population are designated "X" (AGAT-CAATTG; SEQ ID NO:16) and "Y" (AGACCGATTG; SEQ ID NO:17)(FIG. 2A). The nucleic acid sequences differ at two positions (positions 4 and 6 indicated by "*"). The "top" strand of nucleic acids X and Y are designated "1+" and "3+," respectively, and the "bottom" strand of nucleic acids X and Y are designated "2−" and "4−," respectively.

FIG. 2B shows the possible combinations of the four nucleic acid strands. Of the six possible strand combinations, only the combination of 1+/2−, 1+/4−, 2−/3+, or 3+/4− comprise the required top and bottom strand of a partially complementary nucleic acid population. Of these top/bottom sequence combinations, only 1+/4− or 2−/3+ comprise an example of a partially complementary nucleic acid population of two different molecules because only these combinations have complementary sequences that differ by at least one nucleotide. The remaining combinations, 1+/2− and 2+/4−, contain exactly complementary sequences and therefore do not comprise a partially complementary nucleic acid population of the invention.

In the above described example of a population of two different molecules, a partially complementary population of nucleic acid molecules excluded combinations of strands that differ by one or more nucleotides but which are the same sense, for example, 1+/3+ or 2−/4−. However, it is understood that such a combination of same stranded nucleic acids can be included in a larger population, so long as the population contains at least one bottom strand and at least one top strand. For example, if a third nucleic acid "Z," with strands 5+ and 6− is included, the combinations 1+/3+/6− or 2−/4−/5+ would comprise a partially complementary nucleic acid population. Similarly, any number of nucleic acids and their corresponding top and bottom strands can be combined to generate a partially complementary nucleic acid population of the invention so long as the population contains at least one top strand and at least one bottom strand and so long as the population contains no members that are the exact complement.

The populations of nucleic acids of the invention can be about 3 or more, about 4 or more, about 5 or more, about 6 or more, about 7 or more, about 8 or more, about 9 or more, about 10 or more, about 12 or more, about 15 or more, about 20 or more, about 25 or more about 30 or more, about 40 or more, about 50 or more, about 75 or more, about 100 or more, about 150 or more, about 200 or more, about 250 or more, about 300 or more, about 350 or more, about 400 or more, about 450 or more, about 500 or more, or even about 1000 or more different nucleic acid molecules. A population can also contain about 2000 or more, about 5000 or more, about $1 \times 10^4$ or more, about $1 \times 10^5$ or more, about $1 \times 10^6$ or more, about $1 \times 10^7$ or more, or even about $1 \times 10^8$ or more different nucleic acids. One skilled in the art can readily determine a desirable population to include in invention methods depending on the nature of the desired reassortment experiment outcome and the available screening methods, as disclosed herein.

As used herein, a "polymerase" refers to an enzyme that catalyzes the formation of polymers of nucleotides, that is, polynucleotides. A polymerase useful in the invention can be derived from any organism or source, including animal, plant, bacterial and viral polymerases. A polymerase can be a DNA polymerase, RNA polymerase, or a reverse transcriptase capable of transcribing RNA into DNA.

As used herein the term "proofreading" describes the property of an enzyme where a nucleotide, such as, a mismatch nucleotide, can be removed by a 3'-to-5' exonuclease activity and replaced by, typically, a base-paired nucleotide.

As used herein, a "recombinant" polynucleotide refers to a polynucleotide that comprises sequence information from at least two different polynucleotides.

As used herein the term "related polynucleotides" means that regions or areas of the polynucleotides are identical and regions or areas of the polynucleotides are non-identical.

As used herein the term DNA "reassortment" is used herein to indicate a redistribution of sequence variations between substantially homologous but non-identical sequences.

As used herein the term "replicon" refers to a genetic unit of replication including a length of polynucleotide and its site for initiation of replication.

As used herein the term "sequence diversity" refers to the abundance of non-identical polynucleotides. The term "increasing sequence diversity in a population" means to increase the abundance of non-identical polynucleotides in a population.

As used herein the term "sequence variant" is used herein refers to a molecule (DNA, RNA polypeptide, and the like) with one or more sequence differences compared to a reference molecule. For example, the sum of the separate independent mismatch resolution events that occur throughout the heteroduplex molecule during the GRAMMR process results in reassortment of sequence information throughout that molecule. The sequence information will reassort in a variety of combinations to generate a complex library of "sequence variants".

As used herein the term "strand cleavage activity" or "cleavage" refers to the breaking of a phosphodiester bond in the backbone of the polynucleotide strand, as in forming a nick. Strand cleavage activity can be provided by an enzymatic agent, such agents include, but are not limited to CEL I, T4 endonuclease VII, T7 endonuclease I, S1 nuclease, BAL-31 nuclease, FEN1, cleavase, pancreatic DNase I, SP nuclease, mung bean nuclease, and nuclease P1; by a chemical agent, such agents include, but are not limited to potassium permanganate, tetraethylammonium acetate, sterically bulky photoactivatable DNA intercalators, [Rh(bpy)2(chrysi)]3+, osmium tetroxide with piperidine, and hydroxylamine with piperidine; or by energy in the form of ionizing radiation, or kinetic radiation.

As used herein the term "sufficient time" refers to the period time necessary for a reaction or process to render a desired product. For the present invention, the determination of sufficient time is well within the knowledge of those of ordinary skill in the art. It is noted that "sufficient time" can vary widely, depending on the desires of the practitioner, without impacting on the functionality of the reaction, or the quality of the desired product.

As used herein the term "wild-type" means that a nucleic acid fragment does not contain any mutations. A "wild-type" protein means that the protein will be active at a level of activity found in nature and typically will be the amino acid sequence found in nature. In an aspect, the term "wild type" or "parental sequence" can indicate a starting or reference sequence prior to a manipulation of the invention.

In the polypeptide notation used herein, the left-hand direction is the amino terminal direction and the right-hand direction is the carboxy-terminal direction, in accordance with standard usage and convention. Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction.

DETAILED DESCRIPTION OF THE INVENTION

The present invention provides an in vitro method of making sequence variants from at least one heteroduplex polynucleotide wherein the heteroduplex has at least two non-complementary nucleotide base pairs, the method comprising: preparing at least one heteroduplex polynucleotide; combining said heteroduplex polynucleotide with an effective amount of an agent or agents with exonuclease activity, polymerase activity and strand cleavage activity; and allowing sufficient time for the percentage of complementarity to increase, wherein at least one or more variants are made.

Another aspect of the present invention is where the heteroduplex polynucleotides are circular, linear or a replicon.

Another aspect of the present invention is where the desired variants have different amounts of complementarity.

Another aspect of the present invention is where the exonuclease activity, polymerase activity, and strand cleavage activity is added sequentially, or concurrently.

Another aspect of the present invention provides the addition of ligase activity, provided by agents such as, T4 DNA ligase, *E. coli* DNA ligase, or Taq DNA ligase.

Another aspect of the present invention is where the strand cleavage activity is provided by an enzyme, such as, CEL I, T4 endonuclease VII, T7 endonuclease I, S1 nuclease, BAL-31 nuclease, FEN1, cleavase, pancreatic DNase I, SP nuclease, mung bean nuclease, and nuclease P1; a chemical agent, such as, potassium permanganate, tetraethylammonium acetate, sterically bulky photoactivatable DNA intercalators, [Rh(bpy)2(chrysi)]3+, osmium tetroxide with piperidine, and hydroxylamine with piperidine or a form of energy, such as, ionizing or kinetic radiation.

Another aspect of the present invention is where polymerase activity is provided by Pol beta.

Another aspect of the present invention is where both polymerase activity and 3' to 5' exonuclease activity is provided T4 DNA polymerase, T7 DNA polymerase, *E. coli* Pol 1, or Pfu DNA polymerase.

Another aspect of the present invention is where the agent with both polymerase activity and 5' to 3' exonuclease activity is *E. coli* Pol 1.

An embodiment of the present invention is where the effective amount of strand cleavage activity, and exonuclease activity/polymerase activity and ligase activity are provided by CEL I, T4 DNA polymerase, and T4 DNA ligase.

Another aspect of the present invention is where the effective amount of strand cleavage activity, and exonuclease activity/polymerase activity and ligase activity are provided by CEL I, T7 DNA polymerase, and T4 DNA ligase.

Another embodiment of the present invention provides an in vitro method of increasing diversity in a population of sequences, comprising, preparing at least one heteroduplex polynucleotide; combining the heteroduplex polynucleotide with an effective amount of an agent or agents with 3' to 5' exonuclease activity, polymerase activity and strand cleavage activity; and allowing sufficient time for the percentage of complementarity to increase, wherein diversity in the population is increased.

Another embodiment of the present invention provides a method of obtaining a polynucleotide encoding a desired functional property, comprising: preparing at least one heteroduplex polynucleotide; combining said heteroduplex polynucleotide with an effective amount of an agent or agents with exonuclease activity, polymerase activity and strand cleavage activity; allowing sufficient time for the percentage of complementarity between strands of the heteroduplex polynucleotide to increase, wherein diversity in the population is increased; and screening or selecting a population of variants for the desired functional property.

Another embodiment of the present invention provides a method of obtaining a polynucleotide encoding a desired functional property, comprising: preparing at least one heteroduplex polynucleotide; combining said heteroduplex polynucleotide with an effective amount of an agent or agents with exonuclease activity, polymerase activity and strand cleavage activity; allowing sufficient time for the percentage of complementarity between strands of the heteroduplex polynucleotide to increase, wherein diversity in the population is increased; converting DNA to RNA; and screening or selecting a population of ribonucleic acid variants for the desired functional property.

Yet another embodiment of the present invention provides a method of obtaining a polypeptide having a desired functional property, comprising: preparing at least one heteroduplex polynucleotide; combining said heteroduplex polynucleotide with an effective amount of an agent or agents with exonuclease activity, polymerase activity and strand cleavage activity; allowing sufficient time for the percentage of complementarity between strands of said heteroduplex polynucleotide to increase, converting said heteroduplex polynucleotide to RNA, and said RNA to a polypeptide; and screening or selecting a population of polypeptide variants for said desired functional property.

Still another embodiment of the present invention provides a method of obtaining a polynucleotide encoding a desired functional property, comprising: preparing at least one heteroduplex polynucleotide, where the heteroduplex is optionally, about 95%, 90%, 85%, 80%, or 75% identical, and about 1000 KB, 10,000 KB, or 100,000 KB is size; combining said heteroduplex polynucleotide with an effective amount of an agent or agents with exonuclease activity, polymerase activity and strand cleavage activity; allowing sufficient time for the percentage of complementarity between strands of the heteroduplex polynucleotide to increase, screening or selecting for a population of variants having a desired functional property; denaturing said population of variants to obtain single strand polynucleotides; annealing said single strand polynucleotides to form at least one second heteroduplex polynucleotide; combining said second heteroduplex polynucleotide with an effective amount of an agent or agents with exonuclease activity, polymerase activity and strand cleavage activity; and allowing sufficient time for the percentage of complementarity between strands of the heteroduplex polynucleotide to increase.

The present invention is directed to a method for generating an improved polynucleotide sequence or a population of improved polynucleotide sequences, typically in the form of amplified and/or cloned polynucleotides, whereby the improved polynucleotide sequence(s) possess at least one desired phenotypic characteristic (e.g., encodes a polypeptide, promotes transcription of linked polynucleotides, binds a protein, improves the function of a viral vector, and the like) which can be selected or screened for. Such desired polynucleotides can be used in a number of ways such as expression from a suitable plant, animal, fungal, yeast, or bacterial expression vector, integration to form a transgenic plant, animal or microorganism, expression of a ribozyme, and the like.

GRAMMR provides for a process where heteroduplexed DNA strands are created by annealing followed by resolution of mismatches in an in vitro reaction. This reaction begins with cleavage of one strand or the other at or near a mismatch followed by excision of mismatched bases from that strand and polymerization to fill in the resulting gap with nucleotides that are templated to the sequence of the other strand. The resulting nick can be sealed by ligation to rejoin the backbone. The sum of the separate independent mismatch resolution events that occur throughout the heteroduplex molecule will result in reassortment of sequence information throughout that molecule. The sequence information will reassort in a variety of combinations to generate a complex library of sequence variants.

In one embodiment of GRAMMR, a library of mutants is generated by any method known in the art such as mutagenic PCR, chemical mutagenesis, etc. followed by screening or selection for mutants with a desired property. DNA is prepared from the chosen mutants. The DNAs of the mutants are mixed, denatured to single strands, and allowed to anneal. Partially complementary strands that hybridize will have non-base-paired nucleotides at the sites of the mismatches. Treatment with CEL I (Oleykowski et al., 1998; Yang et al., 2000), or a similar mismatch-directed activity, will cause nicking of one or the other polynucleotide strand 3' of each mismatch. (In addition, CEL I can nick 3' of an insertion/deletion resulting in reassortment of insertions/deletions.) The presence of a polymerase containing a 3'-to-5' exonuclease ("proofreading") activity (e.g., T4 DNA Pol) will allow excision of the mismatch, and subsequent 5'-to-3' polymerase activity will fill in the gap using the other strand as a template. A polymerase that lacks 5'-3' exonuclease activity and strand-displacement activity will fill in the gap and will cease to polymerize when it reaches the 5' end of DNA located at the original CEL I cleavage site, thus re-synthesizing only short patches of sequence. Alternatively, the length of the synthesized patches can be modulated by spiking the reaction with a polymerase that contains a 5'-3' exonuclease activity; this nick-translation activity can traverse a longer region resulting in a longer patch of information transferred from the template strand. DNA ligase (e.g., T4 DNA ligase) can then seal the nick by restoring the phosphate backbone of the repaired strand. This process can occur simultaneously at many sites and on either strand of a given heteroduplexed DNA molecule. The result is a randomization of sequence differences among input strands to give a population of sequence variants that is more diverse than the population of starting sequences. These output polynucleotides can be cloned directly into a suitable vector, or they can be amplified by PCR before cloning. Alternatively, the reaction can be carried out on heteroduplexed regions within the context of a double-stranded circular plasmid molecule or other suitable replicon that can be directly introduced into the appropriate host following the GRAMMR reaction. In another alternative, the output polynucleotides can be transcribed into RNA polynucleotides and used directly, for example, by inoculation of a plant viral vector onto a plant, such as in the instance of a viral vector transcription plasmid. The resulting clones are subjected to a selection or a screen for improvements in a desired property. The overall process can then be repeated one or more times with the selected clones in an attempt to obtain additional improvements.

If the output polynucleotides are cloned directly, there is the possibility of incompletely resolved molecules persisting that, upon replication in the cloning host, could lead to two different plasmids in the same cell. These plasmids could potentially give rise to mixed-plasmid colonies. If it is desired to avoid such a possibility, the output polynucleotide molecules can be grown in the host to allow replication/resolution, the polynucleotides isolated and retransformed into new host cells.

In another embodiment, when sequence input from more than two parents per molecule is desired, the above procedure is performed in a cyclic manner before any cloning of output polynucleotides. After GRMMR treatment, the double stranded polynucleotides are denatured, allowed to anneal, and the mismatch resolution process is repeated. After a desired number of such cycles, the output polynucleotides can be cloned directly, introduced into a suitable vector, or they can be amplified by PCR before cloning. The resulting clones are subjected to a selection or a screen for improvements in a desired property.

In another embodiment, a "molecular backcross" is performed to help eliminate the background of deleterious mutations from the desired mutations. A pool of desired mutants' DNA can be mixed with an appropriate ratio of wild-type DNA to perform the method. Clones can be selected for improvement, pooled, and crossed back to wild-type again until there is no further significant change.

The efficiency of the process is improved by various methods of enriching the starting population for heteroduplex molecules, thus reducing the number of unaltered parental-type output molecules. The mismatched hybrids can be affinity purified using aptamers, dyes, or other agents that bind to mismatched DNA. A preferred embodiment is the use of MutS protein affinity matrix (Wagner et al., Nucleic Acids Res. 23(19):3944-3948 (1995); Su et al., Proc. Natl. Acad. Sci. (U.S.A.), 83:5057-5061(1986)) or mismatch-binding but non-cleaving mutants of phage T4 endonuclease VII (Golz and Kemper, Nucleic Acids Research, 1999; 27: e7).

In one embodiment, the procedure is modified so that the input polynucleotides consist of a single strand of each sequence variant. For example, single-stranded DNAs of opposite strandedness are produced from the different parent sequences by asymmetric PCR to generate partially complementary single-stranded molecules. Annealing of the strands with one-another to make heteroduplex is performed as described in Example 1. Alternatively, single-stranded DNAs can be generated by preferentially digesting one strand of each parental double-stranded DNA with Lambda exonuclease followed by annealing the remaining strands to one-another. In this embodiment, the annealing strands have no 100% complementary strand present with which to re-anneal. Hence, there is a lower background of unmodified polynucleotides, that is, "parental polynucleotides" among the output polynucleotides leading to a higher efficiency of reasserting sequence variations. This increased efficiency will be particularly valuable in situations where a screen rather than a selection is employed to test for the desired polynucleotides.

Another method for heteroduplex formation is to mix the double-stranded parent DNAs, denature to dissociate the strands, and allow the single-stranded DNAs to anneal to one-another to generate a population of heteroduplexes and parental homoduplexes. The heteroduplexes can then be selectively enriched by a heteroduplex capture method such as those described above using MutS or a non-cleaving T4 endonuclease VII mutant. Alternatively, the parental homoduplex molecules in the population may be cleaved by restriction enzymes that overlap with sites of mismatch such that they are not cleaved in the heteroduplex but are cleaved in the parental homoduplex molecules. Uncleaved heteroduplex DNA can then be isolated by size fractionation in an agarose gel as was performed to generate full-length plasmid on full-length plasmid heteroduplex DNA molecules as describe in Example 6. Circularization of those full-length heteroduplexed plasmid molecules was then brought about by incubation with DNA ligase.

In another embodiment, the parental, or input, double-stranded polynucleotides are modified by the addition of "clamp" sequences. One input polynucleotide or pool of polynucleotides is amplified by PCR with the addition of a unique sequence in the 5' primer. The other input polynucleotide or pool is amplified by PCR with the addition of a unique sequence in the 3' primer. The clamp sequences can be designed to contain a unique restriction enzyme site for the 5' end of the gene of interest and another for the 3' end such that, at the step of cloning the products of the GRAMMR reassortment, only products with the 5' clamp from the first polynucleotide (or pool) and the 3' end from the second polynucleotide (or pool) will have appropriate ends for cloning. Alternatively, the products of GRAMMR reassortment can be PCR amplified using the unique sequences of the 5' and 3' clamps to achieve a similar result. Hence, there is a lower background of unmodified polynucleotides, that is, "parental polynucleotides" among the output polynucleotide clones leading to a higher efficiency of reasserting sequence variations. This increased efficiency will be particularly valuable in situations where a screen rather than a selection is employed to test for the desired polynucleotides. Optionally, oligonucleotide primers can be added to the GRAMMR reaction that are complementary to the clamp primer sequences such that either parent can serve as the top strand, thus permitting both reciprocal heteroduplexes to participate in the mismatch-resolution reaction.

Another method for generating cyclic heteroduplexed polynucleotides is performed where parental double-stranded DNAs have terminal clamp sequences as described above where the single-stranded clamp sequences extending from one end of the heteroduplex are complementary to single-stranded clamp sequences extending from the other end of the heteroduplex. These complementary, single-stranded clamps are allowed to anneal, thereby circularizing the heteroduplexed DNA molecule. Parental homoduplexes that result from re-annealing of identical sequences have only one clamp sequence and therefore, no complementary single-stranded sequences at their termini with which circularization can occur. Additionally, a DNA polymerase and a DNA ligase can be used to fill-in any gaps in the circular molecules and to seal the nicks in the backbone, respectively, to result in the formation of a population of covalently-closed circular heteroduplex molecules. As the covalently-closed circular heteroduplex molecules will not dissociate into their component strands if subjected to further denaturing conditions, the process of denaturation, circularization, and ligation can be repeated to convert more of the linear double-stranded parental duplexes into closed into closed circular heteroduplexes.

In another embodiment, a region of a single-stranded circular phagemid DNA can be hybridized to a related, but non-identical linear DNA, which can then be extended with a polymerase such as T7 DNA polymerase or T4 DNA polymerase plus T4 gene 32 protein, then ligated at the resulting nick to obtain a circular, double-stranded molecule with heteroduplexed regions at the sites of differences between the DNAs. GRAMMR can then be carried out on this molecule to obtain a library of sequence-reassorted molecules.

Alternately, two single-stranded circular phagemid DNAs of opposite strand polarity relative to the plasmid backbone, and parent gene sequences that are the target of the reassortment are annealed to one and other. A region of extensive mismatch will occur where the phage f1 origin sequences reside. Upon GRAMMR treatment, however, this region of extensive mismatch can revert to either parental type sequence restoring a function f1 origin. These double strained molecules will also contain mismatch regions at the sites of differences between the strands encoding the parent genes of interest. GRAMMR can then be carried out on this molecule to obtain a library of sequence re-assorted molecule.

As discussed in the preceding paragraphs, the starting DNA or input DNA can be of any number of forms. For example, input DNA can be full-length, single stranded and of opposite sense, as is taught in Example 1. Alternatively, the input DNA can also be a fragment of the full-length strand. The input DNAs can be double-stranded, either one or both, or modified, such as by, methylation, phosphorothiolate linkages, peptide-nucleic acid, substitution of RNA in one or both strands, or the like. Either strand of a duplex can be continuous along both strands, discontinuous but contiguous, discontinuous-with overlaps, or discontinuous with gaps.

GRAMMR can also be applied to DNA fragmentation and reassembly-based DNA shuffling schemes. For instance, in methods where gene fragments are taken through cycles of denaturation, annealing, and extension in the course of gene reassembly, GRAMMR can be employed as an intermediate step.

In one such embodiment, the DNA from a gene, or pool of mutants' genes is fragmented by enzymatic, mechanical or chemical means, and optionally a size range of said fragments is isolated by a means such as separation on an agarose gel. The starting polynucleotide, such as a wild-type, or a desired variant, or a pool thereof, is added to the fragments and the mixture is denatured and then allowed to anneal. The annealed polynucleotides are treated with a polymerase to fill in the single stranded gaps using the intact strand as a template. The resulting partially complementary double strands will have non-base-paired nucleotides at the sites of the mismatches. Treatment with CEL I (Oleykowski et al., 1998; Yang et al., 2000) will cause nicking of one or the other polynucleotide strand 3' of each mismatch. Addition of a polymerase containing a 3'-to-5' exonuclease that provides proofreading activity, such as, DNA Pol I, T4 DNA Pol I, will allow excision of the mismatch, and subsequent 5'-to-3' polymerase activity will fill in the gap using the other strand as a template. A DNA ligase, such as, T4 DNA Ligase, can then seal the nick by restoring the phosphate backbone of the repaired strand. The result is a randomization of sequence variation among input strands to give output strands with potentially improved properties. These output polynucleotides can be cloned directly into a suitable vector, or they can be amplified by PCR before cloning. The resulting clones are subjected to a selection or a screen for improvements in a desired property.

In one such embodiment, the DNA from a pool of mutants' genes is fragmented by enzymatic, mechanical or chemical means, or fragments are generated by limited extension of random oligonucleotides annealed to parental templates (U.S. Pat. No. 5,965,408), and optionally a size range of said fragments is isolated by a means such as separation on an agarose gel. The mixture is denatured and then allowed to anneal. The annealed polynucleotides are optionally treated with a polymerase to fill in the single stranded gaps. The resulting partially complementary double-strand fragments will have non-base paired nucleotides at the sites of the mismatches. Treatment with CEL I (Oleykowski et al., 1998; Yang et al., 2000) will cause nicking of one or the other polynucleotide strand 3' of each mismatch. The activity of a polymerase containing a 3'-to-5' exonuclease ("proofreading") activity, such as T4 DNA Polymerase, will allow excision of the mismatch, and subsequent 5'-to-3' polymerase activity will fill in the gap using the other strand as a template. Optionally, DNA ligase, such as, T4 DNA Ligase, can then seal the nick by restoring the phosphate backbone of the repaired strand. The result is a randomization of sequence variation among input strands to give output strands with potentially improved properties. Subsequent rounds of denaturing, annealing, and GRAMMR treatment allows gene reassembly. PCR can be used to amplify the desired portion of the reassembled gene. These PCR output polynucleotides can be cloned into a suitable vector. The resulting clones are subjected to a selection or a screen for the desired functional property.

Another embodiment of the present invention provides starting with a continuous scaffold strand to which fragments of another gene or genes anneal. The flaps and gaps are trimmed and filled as is described in Coco, et al., Nature Biotech 19 (01)354; U.S. Pat. No. 6,319,713, and GRAMMR is performed. In this process, GRAMMR would bring about further sequence reassortment by permitting transfer of sequence information between the template strand and the strand resulting from flap and gap trimming and ligation. This method provides the benefits of incorporating specific sequence patches into one continuous strand followed by GRAMMR of residues that mismatch with the scaffold. By annealing many fragments simultaneously to the same sequence or gene, many individual sites can be addressed simultaneously, thereby allowing reassortment of multiple sequences or genes at once. Unlike the method disclosed by Coco, et al., in the present embodiment, the scaffold is not degraded, rather the duplex can be directly cloned, or amplified by PCR prior to cloning. Exhaustive mismatch resolution will result in a perfectly duplexed DNA. Partial mismatch resolution will result in essentially two different reasserted products per duplex.

As can be appreciated from the present disclosure, GRAMMR can also be applied to a variety of methods that include the annealing of related DNAs as a step in their process. For example, many site-directed mutagenesis protocols call for the annealing of mutant-encoding DNA molecules to a circular DNA in single-stranded form, either phagemid or denatured plasmid. These DNAs are then extended with a polymerase, followed by treatment with ligase to seal the nick, with further manipulation to remove the parental sequence, leaving the desired mutation or mutations incorporated into the parental genetic background. Though these protocols are generally used to incorporate specific mutations into a particular DNA sequence, it is feasible that the GRAMMR process can be applied to the heteroduplexed molecules generated, in such a process to reassort sequence variations between the two strands, thereby resulting in a diverse set of progeny with reasserted genetic variation.

Another embodiment provides for a sequential round of reassortment on a particular region. For example, DNA fragments are annealed to a circular single-strand phagemid DNA, and GRAMMR is performed. The fragments can be treated in order to prevent them from being physically incorporated into the output material. For example, they can be terminated at the 3' end with di-deoxy residues making them non-extendible. Multiple rounds of reassortment can be performed, but only modified molecules from the original input single stranded DNA clone will be recovered. The consequence will be that the DNA fragments used in this reassortment will contribute only sequence information to the final product and will not be physically integrated into the final recoverable product.

In instances where it is desired to resolve only sites of significant mismatch, that is patches of more than about 1 to 3 mismatches, S1 nuclease can be used. S1 nuclease is an endonuclease specific for single-stranded nucleic acids. It can recognize and cleave limited regions of mismatched base pairs in DNA:DNA or DNA:RNA duplexes. A mismatch of at least about 4 consecutive base pairs is generally required for recognition and cleavage by S1 nuclease. Mismatch resolution will not occur if both strands are cleaved, so the DNA must be repaired after the first nick and before the counter-nick. Other nucleases may be preferable for specifically tuning cleavage specificity according to sequence, sequence context, or size of mismatch.

In addition, other means of addressing mismatched residues, such as chemical cleavage of mismatches may be used. Alternatively, one can choose to subject the strands of heteroduplexed DNA to random nicking with an activity such as that exhibited by DNaseI or an agent that cleaves only in duplexed regions. If nick formation occurs in a region of identity between the two genes, the DNA ligase present in the reaction will seal the nick with no net transfer of sequence information. However, if nick formation occurs near a site of mismatch, the mismatched bases can be removed by 3'-5' exonuclease and the gap filled in by polymerase followed by nick sealing by ligase. Alternatively, application of nick-translation through regions of heterogeneity can bring about sequence reassortment. These processes, though not directed exclusively by the mismatch status of the DNA, will serve to transfer sequence information to the repaired strand, and thus result in a reasserted sequence.

GRAMMR can be used for protein, peptide, or aptamer display methods to obtain recombination between library members that have been selected. As fragmentation of the input DNAs is not required for GRAMMR, it may be possible to reassort sequence information between very small stretches of sequence. For instance, DNAs encoding small peptides or RNA aptamers that have been selected for a particular property such as target binding can be reasserted. For annealing to occur between the selected DNA molecules, some level of sequence homology should be shared between the molecules, such as at the 5' and 3' regions of the coding sequence, in regions of the randomized sequence segment that bear similarity because of similar binding activities, or through the biasing of codon wobble-base identity to a particular set of defaults.

Manipulation of the reaction temperature at which GRAMMR is conducted can be useful. For example, lower temperatures will help to stabilize heteroduplexes allowing GRAMMR to be performed on more highly mismatched substrates. Likewise, additives that affect base-pairing between strands, such as salts, PEG, formamide, etc, can be used to alter the stability of the heteroduplex in the GRAMMR, thereby affecting the outcome of the reaction.

In another embodiment, the mismatched double stranded polynucleotides are generated, treated with a DNA glycosylase to form an apurinic or apyrimidinic site, (that is an "AP site") an AP endonuclease activity to cleave the phosphodiester bond, deoxyribulose phosphodiesterase to remove the deoxyribose-phosphate molecules, DNA polymerase β or other DNA polymerase to add a single nucleotide to the 3' end of the DNA strand at the gap, and DNA ligase to seal the gap. The result is a reassortment of sequence variations between input strands to give output strands with potentially improved properties. These output polynucleotides can be cloned directly into a suitable vector, or they can be amplified by PCR before cloning. The resulting clones are subjected to a selection or a screen for improvements in a desired property.

Another embodiment provides for zonal mutagenesis by GRAMMR, that is, random or semi-random mutations at, and in the immediate vicinity of, mismatched residues using nucleotide analogues that have multiple base-pairing potential. This provides for concentration of essentially random mutagenesis at a particular point of interest, and adds another benefit to the present invention. Similar genes with slightly different functions, for example, plant R-genes, enzymes, or the like, will exhibit moderate sequence differences between them in regions that will be important for their own particular activities. Genes that express these activities, such as different substrates, binding partners, regulatory sites, or the like, should have heterogeneity in the regions that govern these functions. Since it is known that the specificity of such functions is associated with these amino acids and their neighbors, GRAMMR mutagenesis might serve to both reassort sequence variation among genes and also direct random mutagenesis to these regions to drive them further and faster evolutionarily, while not disturbing other sequences, such as structural framework, invariant residues, and other such important sites, that are potentially less tolerant to randomization.

Different enzymes with distinct functions will not differ just in the operative regions, such as active sites, regulatory sites, and the like. They are likely to have other differences from one another that arise through genetic drift. Further randomization in the locales of such changes might therefore be considered neutral, minimally important, or deleterious to the outcome of a mutagenesis experiment. In order to direct the random mutagenesis away from such inconsequential sites, and toward sites that might present a better result for random mutagenesis, such as the active site of an enzyme, the codon usage bias of the genes could be manipulated to decrease or increase the overall level of nucleotide complementarity in those regions. If regions of greater complementarity are less susceptible to GRAMMR than regions of lesser complementarity, then the degree of GRAMMER-directed zonal random mutagenesis at a given site can be modulated.

In another embodiment, after heteroduplex molecules are formed, an enzyme with a 3' to 5' exonuclease activity is added such that one strand of each end of the heteroduplex is digested back. At a point at which, on average, a desired amount of 3' to 5' digestion has occurred, dNTPs are added to allow the 5' to 3' polymerase activity from the same or an additional enzyme to restore the duplex using the opposite strand as a template. Thus mismatches in the digested regions are resolved to complementarity. Optionally, the resultant duplexes are purified, denatured and then allowed to anneal. The process of digestion, then polymerization is repeated resulting in new chimeric sequences. Additional cycles of the process can be performed as desired. Output duplex molecules are cloned and tested for the desired functional property. This process requires no fragmentation and reassembly. In addition, this process requires no endonucleolytic cleavages.

In another embodiment, after the heteroduplex molecules are formed, an enzyme with a 5' to 3' exonuclease activity, such as, T7 Gene6 Exonuclease as disclosed in Enger, M J and Richardson, C C, J Biol Chem 258(83)11197), is added such that one strand of each end of the heteroduplex is digested. At a point at which, on average, a desired amount of 5' to 3' digestion has occurred, the reaction is stopped and the exonuclease inactivated. Oligonucleotide primers complementary to the 5' and 3' ends of the target polynucleotides are added and annealed. A DNA polymerase, such as, T4 DNA Polymerase, a DNA ligase and dNTPs are added to allow the 5' to 3' polymerase activity to extend the primers and restore the duplex using the opposite strand as a template, with ligase sealing the nick. Thus mismatches in the digested regions are resolved to complementarity. Optionally, the resultant duplexes are purified, denatured and then allowed to anneal. The process of digestion then polymerization is repeated resulting in new chimeric sequences. Additional cycles of the process can be performed as desired. Output duplex molecules are cloned and tested for the desired functional property. This process requires no fragmentation and reassembly. In addition, this process requires no endonucleolytic cleavages.

In the current invention the random reassortment occurs in an in vitro DNA mismatch-resolution reaction. This method does not require any steps of "gene reassembly" that serve as the foundation for the earlier mutation reassortment ("shuffling") methods. Instead, it is based upon the ability of a reconstituted or artificial DNA mismatch resolving system to transmit sequence variations from one or more strands of DNA into another DNA strand by hybridization and mismatch resolution in vitro.

In general, standard techniques of recombinant DNA technology are described in various publications, e.g., (Ausubel, 1987; Ausubel, 1999; Sambrook et al., 1989), each of which is incorporated herein in their entirety by reference. Polynucleotide modifying enzymes were used according to the manufacturers recommendations. If desired, PCR amplimers for amplifying a predetermined DNA sequence may be chosen at the discretion of the practitioner.

It is noted that each of the activities taught in the present invention that are involved in the GRAMMR reaction can be interchanged with a functional equivalent agent with similar activity, and that such changes are within the scope of the present invention. For instance, as was indicated in Example 2, Taq DNA ligase could substitute for T4 DNA ligase. Other ligases can be substituted as well, such as E. coli DNA ligase. Likewise, as shown in Examples 2 and 8, respectively, Pfu polymerase and T7 DNA polymerase can be substituted for T4 DNA polymerase. Other enzymes with appropriate exonuclease activity with or without associated polymerase can function in place of any of these enzymes for the exonuclease activity needed for the GRAMMR reaction. In a similar way, any polymerase with functionally equivalent activity to those demonstrated to work for GRAMMR can be used for substitution. These include E. coli Pol 1, the Klenow fragment of E. coli Pol 1, polymerase beta, among many others.

Strand cleavage may be brought about in a number of ways. In addition to CEL I, a number of functionally equivalent, and potentially homologous activities found in extracts from a variety of plant species (Oleykowski, Nucleic Acids Res 1998;26:4597-602) may be used. Other mismatch-directed endonucleases such as T4 endonuclease VII, T7 endonuclease I, and SP nuclease (Oleykowski, Biochemistry 1999; 38: 2200-5) may be used. Other nucleases which attack single stranded DNA can be used, such as S1 nuclease, FEN1, cleavase, mung bean nuclease, and nuclease P1. Enzymes that make random cleavage events in DNA, such as pancreatic DNase I may also be substituted for the strand cleaving activity in GRAMMR. A number of methods for bringing about strand cleavage through other means are also envisioned. These include potassium permanganate used with tetraethylammonium acetate, the use of sterically bulky photoactivatable DNA intercalators such as [Rh(bpy)2(chrysi)]3+, osmium tetroxide with piperidine alkaloid, and hydroxylamine with piperidine alkaloid, as well as the use of radiation energy to bring about strand breakage.

CEL I is a mismatch endonuclease isolated from celery. The use of CEL I in a diagnostic method for the detection of mutations in targeted polynucleotide sequences, in particular, those associated with cancer, is disclosed in U.S. Pat. No. 5,869,245. Methods of isolating and preparing CEL I are also disclosed in this patent. However, there is no disclosure in this patent relating to the use of CEL I in DNA sequence reassortment.

The nucleic acid molecules that encode CEL I are disclosed in PCT Application Publication No. WO 01/62974 A1. As with U.S. Pat. No. 5,869,245, the use of CEL I in a diagnostic method for the detection of mutations in targeted polynucleotide sequences associated with cancer is disclosed. Also similarly, there is no disclosure relating to the use of CEL I in DNA reassortment.

The reactivity of Endonuclease VII of phage T4 with DNA-loops of eight, four, or one nucleotide, or any of 8 possible base mismatches in vitro is disclosed in "Endonuclease VII of Phage T4 Triggers Mismatch Correction in Vitro" Solaro, et al., J Mol Biol 230(93)868. The publication reports a mechanism where Endonuclease VII introduces double stranded breaks by creating nicks and counternicks within six nucleotides 3' of the-mispairing. The publication discloses that a time delay between the occurrence of the first nick and the counternick was sufficient to allow the 3'-5' exonuclease activity of gp43 to remove the mispairing and its polymerase activity to fill in the gap before the occurrence of the counternick. Nucleotides are erased from the first nick, which is located 3' of the mismatch on either strand and stops 5' of the mismatch at the first stable base-pair. The polymerase activity proceeds in the 5' to 3' direction towards the initial nick, which is sealed by DNA ligase. As a result, very short repair tracks of 3 to 4 nucleotides extend across the site of the former mismatch. The publication concludes with a discussion regarding the various activities Endonuclease VII may have within phage T4. However, the publication does not disclose any practical utility for Endonuclease VII outside of phage T4, and there is no disclosure regarding its applicability in DNA reassortment.

A method for creating libraries of chimeric DNA sequences in vivo in *Escherichia coli* is disclosed in *Nucleic Acids Research,* 1999, Vol 27, No. 18, e18, Volkov, A. A., Shao, Z., and Arnold, F. H. The method uses a heteroduplex formed in vitro to transform E. coli where repair of regions of non-identity in the heteroduplex creates a library of new, recombined sequences composed of elements of each parent. Although the publication discloses the use of this method as a convenient addition to existing DNA recombination methods, that is, DNA shuffling, the disclosed method is limited to the in vivo environment of E. coli. The publication states that there is more than one mechanism available for mismatch repair in *E. coli,* and that the 'long patch' repair mechanism, which utilizes the MutS/L/H enzyme system, was probably responsible for the heteroduplex repair.

CITED REFERENCES

1. Arkin, A. P. and Youvan, D. C. (1992) An algorithm for protein engineering: simulations of recursive ensemble mutagenesis. *Proc Natl Acad Sci U S A,* 89, 7811-7815.
2. Ausubel, F. M. (1987) *Current protocols in molecular biology.* Published by Greene Pub. Associates and Wiley-Interscience: J. Wiley, New York.
3. Ausubel, F. M. (1999) *Short protocols in molecular biology: a compendium of methods from Current protocols in molecular biology.* Wiley, New York.
4. Barnes, W. M. (1994) PCR amplification of up to 35-kb DNA with high fidelity and high yield from lambda bacteriophage templates. *Proc Natl Acad Sci USA,* 91, 2216-2220.
5. Bartel, D. P. and Szostak, J. W. (1993) Isolation of new ribozymes from a large pool of random sequences. *Science,* 261, 1411-1418.
6. Cadwell, R. C. and Joyce, G. F. (1992) Randomization of genes by PCR mutagenesis. *PCR Methods Appl,* 2, 28-33.
7. Calogero, S., Bianchi, M. E. and Galizzi, A. (1992) In vivo recombination and the production of hybrid genes. *FEMS Microbiol Lett,* 76, 41-44.
8. Caren, R., Morkeberg, R. and Khosla, C. (1994) Efficient sampling of protein sequence space for multiple mutants. *Biotechnology* (N Y), 12, 517-520.
9. Delagrave, S., Goldman, E. R. and Youvan, D. C. (1993) Recursive ensemble mutagenesis. *Protein Eng,* 6, 327-331.
10. Delagrave, S. and Youvan, D. C. (1993) Searching sequence space to engineer proteins: exponential ensemble mutagenesis. *Biotechnology* (N Y), 11, 1548-1552.
11. Goldman, E. R. and Youvan, D. C. (1992) An algorithmically optimized combinatorial library screened by digital imaging spectroscopy. *Biotechnology* (N Y), 10, 1557-1561.
12. Gram, H., Marconi, L. A., Barbas, C. F. d., Collet, T. A., Lerner, R. A. and Kang, A. S. (1992) In vitro selection and affinity maturation of antibodies from a naive combinatorial immunoglobulin library. *Proc Natl Acad Sci USA,* 89, 3576-3580.
13. Hayashi, N., Welschof, M., Zewe, M., Braunagel, M., Dubel, S., Breitling, F. and Little, M. (1994) Simultaneous mutagenesis of antibody CDR regions by overlap extension and PCR. *Biotechniques,* 17, 310, 312, 314-315.
14. Hermes, J. D., Blacklow, S. C. and Knowles, J. R. (1990) Searching sequence space by definably random mutagenesis: improving the catalytic potency of an enzyme. *Proc Natl Acad Sci USA,* 87, 696-700.
15. Holland, J. H. (1992) Adaptation in natural and artificial systems: an introductory analysis with applications to biology, control, and artificial intelligence. MIT Press, Cambridge, Mass.
16. Ji, G. and Silver, S. (1992) Regulation and expression of the arsenic resistance operon from *Staphylococcus aureus* plasmid pI258. *J Bacteriol,* 174, 3684-3694.
17. Kauffman, S. A. (1993) *The origins of order self-organization and selection in evolution.* Oxford University Press, New York.
18. Marton, A., Delbecchi, L. and Bourgaux, P. (1991) DNA nicking favors PCR recombination. *Nucleic Acids Res,* 19, 2423-2426.
19. Meyerhans, A., Vartanian, J. P. and Wain-Hobson, S. (1990) DNA recombination during PCR. *Nucleic Acids Res,* 18, 1687-1691.
20. Nissim, A., Hoogenboom, H. R., Tomlinson, I. M., Flynn, G., Midgley, C., Lane, D. and Winter, G. (1994) Antibody fragments from a 'single pot' phage display library as immunochemical reagents. *Embo J,* 13, 692-698.
21. Oleykowski, C. A., Bronson Mullins, C. R., Godwin, A. K. and Yeung, A. T. (1998) Mutation detection using a novel plant endonuclease. *Nucleic Acids Res,* 26, 4597-4602.
22. Oliphant, A. R., Nussbaum, A. L. and Struhl, K. (1986) Cloning of random-sequence oligodeoxynucleotides. *Gene,* 44, 177-183.
23. Sambrook, J., Maniatis, T. and Fritsch, E. F. (1989) *Molecular cloning: a laboratory manual.* Cold Spring Harbor Laboratory, Cold Spring Harbor, N.Y.
24. Stemmer, W. P. (1994a) DNA shuffling by random fragmentation and reassembly: in vitro recombination for molecular evolution. *Proc Natl Acad Sci USA,* 91, 10747-10751.
25. Stemmer, W. P. (1994b) Rapid evolution of a protein in vitro by DNA shuffling. *Nature,* 370, 389-391.
26. Stemmer, W. P., Morris, S. K. and Wilson, B. S. (1993) Selection of an active single chain Fv antibody from a protein linker library prepared by enzymatic inverse PCR. *Biotechniques,* 14, 256-265.
27. Winter, G., Griffiths, A. D., Hawkins, R. E. and Hoogenboom, H. R. (1994) Making antibodies by phage display technology. *Annu Rev Immunol,* 12, 433-455.
28. Yang, B., Wen, X., Kodali, N. S., Oleykowski, C. A., Miller, C. G., Kulinski, J., Besack, D., Yeung, J. A., Kowalski, D. and Yeung, A. T. (2000) Purification, cloning, and characterization of the CEL I nuclease. *Biochemistry,* 39, 3533-3541.

The following non-limiting examples are provided to illustrate the present invention.

EXAMPLE 1

Cleavage of Mismatched DNA Substrate by CEL I

This example teaches the preparation of CEL I enzyme and its use in the cleavage of mismatched DNA substrate.

CEL I enzyme was prepared from celery stalks using the homogenization, ammonium sulfate, and Concanavalin A-Sepharose protocol described by Yang et al. (*Biochemistry,* 39:3533-3541 (2000), incorporated herein by reference. A 1.5 kg sample of chilled celery stalks was homogenized with a juice extractor. One liter of juice was collected, adjusted to 100 mM Tris-HCL, pH 7.7 with 100 micromolar phenylmethylsulfonyl fluoride (PMSF), and filtered through two layers of miracloth. Solid $(NH_4)_2SO_4$ was slowly added to 25% saturation while stirring on ice. After 30 minutes, the suspension was centrifuged at 27,000 g for 1.5 hours at 4° C. The supernatants were collected and adjusted with solid $(NH_4)_2SO_4$ to 80% saturation while stirring on ice followed by centrifugation at 27,000 g for 2 hours. The pellets were re-suspended in buffer B (0.1 M Tris-HCL, pH 7.7, 0.5 M KCl, 100 micromolar PMSF) and dialyzed against the same buffer.

Conconavalin A (ConA) Sepharose affinity chromatography was performed by first incubating the dialyzed sample with 2 ml of ConA resin overnight with gentle agitation. The ConA resin was then packed into a 0.5 cm diameter column and washed with several column volumes of buffer B. Elution was performed using 0.3 M alpha-methyl-mannoside in buffer B. Fractions were collected in 1 ml aliquots. Fractions were assayed for mismatch cleavage activity on a radiolabeled mismatch substrate by incubating 0.1 microliter of each fraction with the mismatched probe in buffer D (20 mM Tris-HCL, pH 7.4, 25 mM KCL, 10 mM $MgCl_2$) for 30 minutes at 45° C. as described by Oleykowski et al. (Nucleic Acids Research 26: 4597-4602 (1998), incorporated herein by reference. Reaction products were visualized by separation on 10% TBE-PAGE gels containing 7% urea (Invitrogen), followed by autoradiography. Aliquots of the CEL I fractions having mismatch cleavage activity were stored frozen at −20° C. A series of five-fold dilutions of CEL I fraction #5 were then analyzed for mismatch cleavage of radiolabeled mismatch substrate. Reactions were performed either in buffer D, New England BioLabs (NEB) T4 DNA ligase buffer (50 mM Tris-HCL, pH 7.5, 10 mM $MgCl_2$, 10 mM dithiothreitol (DTT), 1 mM ATP, 25 microgram/ml BSA), or Gibco/BRL T4 DNA ligase buffer (50 mM Tris-HCL, pH 7.6, 10 mM $MgCl_2$, 1 mM DTT, 1 mM ATP, 5% (w/v) polyethylene glycol-8000). Reaction products were visualized as above. Cleavage activity in buffer D and in NEB T4 DNA ligase buffer were found to be roughly equivalent, whereas cleavage in the PEG-containing Gibco/BRL ligase buffer was enhanced by five to ten-fold compared to the other buffers.

Additional analysis of CEL I activity was carried out using defined heteroduplex DNAs from two different Green Fluorescent Protein (GFP) genes as substrate. This GFP heteroduplex substrate was prepared by annealing single stranded DNAs corresponding to cycle 3 GFP on the sense strand and wild-type GFP on the antisense strand. The single-stranded DNAs had been synthesized by asymmetric PCR and isolated by agarose gel electrophoresis. After annealing by heating to 90° C. and cooling in the presence of 1×NEB restriction enzyme buffer 2 (10 mM Tris-HCL, pH 7.9, 10 mM $MgCl_2$, 50 mM NaCl, 1 mM dithiothreitol), the heteroduplex DNA was isolated by agarose gel electrophoresis followed by excision of the heterduplex band and extraction using Qiaquick DNA spin columns. A total of twenty eight mismatches, one or two nucleotides in length, occur throughout the length of the heteroduplex molecule. The distribution of the mismatches ranges from small clusters of several mismatches separated by one or two nucleotides to mismatches separated by more than thirty base pairs on either side.

A series of three-fold dilutions of CEL I in 1×NEB T4 DNA ligase buffer were prepared and one microliter aliquots of each were incubated in two separate series of 10 microliter reactions, each containing as substrate either 0.5 microgram of a supercoiled plasmid preparation or one hundred nanograms of the cycle3,/wild-type GEP heteroduplex. All reactions took place in 1×NEB T4 DNA ligase buffer. Reactions were incubated at 45° C. for 30 minutes and run on 1.5% TBE-agarose gel in the presence of ethidium bromide.

Treatment of the supercoiled plasmid preparation with increasing amounts of CEL I resulted in the conversion of supercoiled DNA to nicked circular, then linear molecules, and then to smaller fragments of DNA of random size. Treatment of the mismatched GFP substrate with the CEL I preparation resulted in the digestion of the full-length heteroduplex into laddered DNA bands which are likely to represent cleavage on opposite DNA strands in the vicinity of clusters of mismatches. Further digestion resulted in the conversion of the mismatched GFP substrate to smaller DNAs that may represent a limit digest of the heteroduplex DNA by the CEL I preparation.

EXAMPLE 2

Conservation of Full Length GFP Gene with Mismatch Resolution Cocktails

This example teaches various mismatch resolution cocktails that conserve the full length GFP Gene.

Mismatched GFP substrate was treated with various concentrations of CEL I in the presence of cocktails of enzymes that together constitute a synthetic mismatch resolution system. The enzymes used were CEL I, T4 DNA polymerase, Taq DNA polymerase and T4 DNA ligase. CEL I activity should nick the heteroduplex 3' of mismatched bases. T4 DNA polymerase contains 3'-5' exonuclease for excision of the mismatched base from the nicked heteroduplex. T4 DNA polymerase and Taq DNA polymerase contain DNA polymerase capable of filling the gap. T4 DNA ligase seals the nick in the repaired molecule. Taq DNA polymerase also has 5' flap-ase activity.

Matrix experiments were performed to identify the reaction conditions that would serve to resolve mismatches in the GFP heteroduplex substrate. In one experiment, cycle 3/wild-type GFP heteroduplex was incubated in a matrix format with serial dilutions of CEL I fraction number five (described above) at eight different concentrations. Each reaction contained 100 nanograms of heteroduplex substrate and 0.2 microliters of T4 DNA ligase (Gibco BRL) in 1×NEBT4 DNA ligase buffer and dNTPs at 250 micromolar each, in a reaction volume of 10 microliters. In all, the matrix contained 96 individual reactions. One full set of reactions was incubated at room temperature for 30 minutes while another full set was incubated at 37° C. for 30 minutes.

After incubation, PCR was used to amplify the GFP gene from each reaction. Aliquots from each PCR were then digested with HindIII and HpaI and electrophoresed on 3% agarose gels with ethidium bromide. Only cycle 3 GFP has a HindIII site and only wild-type encodes a HpaI site.

If DNA mismatch resolution occurred at either the HindIII or HpaI mismatched sites, then a proportion of the PCR product would be expected to contain both sites, yielding a novel band. The band was observed in all samples, including the negative control samples that had neither CEL I, nor T4 DNA polymerase, nor Taq DNA polymerase. The results suggested that a basal level of background recombination may have occurred at some point in the experiment other than in the GRAMMR reaction; possibly in the PCR step. PCR-mediated recombination is known to occur at some frequency between related sequences during amplification [reference Paabo, et al., DNA damage promotes jumping between templates during enzymatic amplification. J Biol Chem 265(90)4718-4721].

In another experiment, 200 nanograms of cycle 3/wild-type GFP heteroduplex was treated with CEL I and T4 DNA polymerase in various concentrations along with 2.5 units of Taq DNA polymerase in the presence or absence of T4 DNA ligase (0.2 units; Gibco BRL). Each reaction contained 1×NEB T4 DNA ligase buffer with 0.05 mM each dNTP in a final volume of 20 microliters. Reactions were incubated for 30 minutes at 37° C. and 10 microliters were run on a 2% TBE-agarose gel in the presence of ethidium bromide. Results showed that in the presence of DNA ligase, but in the absence of T4 DNA polymerase, increasing amounts of CEL I caused greater degradation of the heteroduplexed DNA, but that this effect could be counteracted by increasing the amount of T4 DNA polymerase in the reaction. These results indicated that the various components of the complete reaction could act together to conserve the integrity of the full-length gene through DNA mismatch resolution.

Another matrix experiment was conducted to expand on these results and to identify additional conditions for DNA mismatch resolution for this synthetic system. 60 nanograms of cycle3/wild-type GFP heteroduplex were treated with CEL I and T4 DNA polymerase at various concentrations in the presence of 2.5 units of Taq DNA polymerase and 0.2 units of T4 DNA ligase in 1×NEB T4 DNA ligase buffer containing 0.5 mM of each dNTP in a reaction volume of 10 microliters. Each set of reactions was incubated for 1 hour at either 20° C., 30° C., 37° C., or at 45° C. All reactions were then run on a 1.5% TBE-agarose gels in the presence of ethidium bromide. The results showed that the GFP heteroduplex was cleaved into discrete fragments by the CEL I preparation alone. The success of DNA mismatch resolution was initially gauged by the degree to which the apparent full-length integrity of the GFP sequence was maintained by the other components of the mismatch resolution system in the presence of CEL I. Conditions of enzyme concentration and temperature were identified that conserved a high proportion of the DNA as full-length molecules in this assay. Namely, one microliter of the CEL I fraction five preparation (described in Example 1) with one microliter (1 unit) of the T4 DNA polymerase in the presence of the other reaction components which were held constant in the experiment. It was found that as the reaction temperature increased, the degradative activity of CEL I increased accordingly. Furthermore, it was shown that the other components of the repair reaction acted to conserve the integrity of the full-length DNA at 20° C., 30° C., and 37° C., but was remarkably less efficient at conserving the full-length DNA at 45° C. From these results, we concluded that under these experimental conditions, incubation at 45° C. was not optimal for the process of GRAMMR, and that incubation at 20° C., 30° C., and 37° C. were permissible.

Another experiment was performed in which alternative enzymes were used for the DNA mismatch resolution reaction. Instead of T4 DNA ligase, Taq DNA ligase was used. Pfu DNA polymerase (Stratagene) was employed in a parallel comparison to a set of reactions that contained T4 DNA polymerase as the 3' exonuclease/polymerase. Reactions were carried out in Taq DNA ligase buffer containing 8 units of Taq DNA ligase (NEB), 2.5 units Taq DNA polymerase, 0.5 mM of each dNTP, various dilutions of CEL I, and either T4 DNA polymerase or Pfu DNA polymerase). Reactions were run on a 1.5% TBE-agarose gels in the presence of ethidium bromide. It was found that in the presence of the Pfu DNA polymerase, Taq DNA polymerase, and Taq DNA ligase, the full-length integrity of the CEL I-treated substrate DNA was enhanced compared to DNA incubated with CEL I alone. This result shows that enzymes with functionally equivalent activities can be successfully substituted into the GRAMMR reaction.

EXAMPLE 3

Restoration of Restriction Sites to GFP Heteroduplex DNA after DNA Mismatch Resolution (GRAMMR)

This experiment teaches the operability of genetic reassortment by DNA mismatch resolution (GRAMMR) by demonstrating the restoration of restriction sites.

The full-length products of a twenty-fold scale-up of the GRAMMR reaction, performed at 37° C. for one hour, using the optimal conditions found above (the 1× reaction contained sixty nanograms of heteroduplex DNA, one microliter of CEL I fraction five (described in Example 1), one unit T4 DNA polymerase in the presence of 2.5 units of Taq DNA polymerase and 0.2 units of T4 DNA ligase in 1×NEB T4 DNA ligase buffer containing 0.5 mM of each dNTP in a reaction volume of 10 microliters) were gel-isolated and subjected to restriction analysis by endonucleases whose recognition sites overlap with mismatches in the GFP heteroduplex, thereby rendering those sites in the DNA resistant to restriction enzyme cleavage. The enzymes used were BamHI, HindIII, HpaI, and XhoI. Negative controls consisted of untreated GFP heteroduplex. Positive controls consisted of Cycle 3 or wild type GFP sequences, individually. All controls were digested with the same enzymes as the product of the DNA mismatch resolution reaction. All samples were run on a 2% TBE-agarose gel in the presence of ethidium bromide.

After treatment with the mismatch resolution cocktail, a proportion of the DNA gained sensitivity to BamHI and XhoI restriction endonucleases, indicating that DNA mismatch resolution had occurred. The HpaI-cut samples could not be interpreted since a low level of cleavage occurred in the negative control. The HindIII, BamHI and XhoI sites displayed different degrees of cleavage in the GRAMMR-treated samples. Restoration of the XhoI site was more extensive than that of the BamHI site, which was in turn, more extensive than restoration at HindIII site.

The extent to which cleavage occurs is indicative of the extent to which mismatches in the DNA have been resolved at that site. Differences in mismatch resolution efficiency may relate to the nature or density of mismatches present at those sites. For example, the XhoI site spans a three-mismatch cluster, whereas the BamHI site spans two mismatches and the HindIII site spans a single mismatch.

EXAMPLE 4

GRAMMR-Reassorted GFP Genes

This example demonstrates that GRAMMR can reassort sequence variation between two gene sequences in a heteroduplex and that there are no significant differences in GRAMMR products that were directly. cloned, or PCR amplified prior to cloning.

The GRAMMR-treated DNA molecules of Example 3 were subsequently either directly cloned by ligation into pCR-Blunt II-TOPO (Invitrogen), or amplified by PCR and ligated into pCR-Blunt II-TOPO according to the manufacturer's instructions, followed by transformation into E. coli. After picking individual colonies and growing in liquid culture, DNA was prepared and the sequences of the GFP inserts were determined. As negative controls, the untreated GFP heteroduplex substrate was either directly cloned or PCR amplified prior to cloning into the plasmid.

In GRAMMR, reassortment of sequence information results from a process of information transfer from one strand to the other. These sites of information transfer are analogous to crossover events that occur in recombination-based DNA shuffling methods. For the purposes of relating the results of these reassortment experiments, however, the GRAMMR output sequences are described in terms of crossovers. Sequences of twenty full-length GFP clones that were derived from the GRAMMR-treated GFP genes were analyzed. Four of these clones were derived from DNA that had been directly cloned into pZeroBlunt [ref] following GRAMMR treatment (no PCR amplification). The other sixteen sequences were cloned after PCR amplification.

Analysis of these full-length GFP sequences revealed that all twenty sequences had undergone sequence reassortment having between one and ten crossovers per gene. A total of 99 crossovers were found in this set of genes, giving an average of about 5 crossovers per gene. With the distance between the first and last mismatches of about 590 nucleotides, an overall frequency of roughly one crossover per 120 base-pairs was calculated. Within this set of twenty clones, a total of seven point mutations had occurred within the sequences situated between the PCR primer sequences, yielding a mutation frequency of roughly 0.05%.

Thirty-five clones that had not been subjected to GRAMMR treatment were sequenced. Of these controls, fourteen were derived from direct cloning and twenty-one were obtained after PCR amplification using the GFP heteroduplex as template. Of these thirty-five non-GRAMMR treated control clones, eight were recombinants, ranging from one to three crossovers, with most being single crossover events. A total of twenty-five point mutations had occurred within the sequences situated between the PCR primers, yielding a mutation frequency of roughly 0.1%.

No significant differences were observed between the GRAMMR-treated products that were either directly cloned or PCR amplified. Notably, though, in the non-GRAMMR-treated controls, the frequency of recombinants was higher in the PCR amplified DNAs than in the directly cloned DNAs. This higher frequency is consistent with results obtained by others in which a certain level of recombination was found to be caused by "jumping PCR." [Paabo, et al., DNA damage promotes jumping between templates during enzymatic amplification. J Biol Chem 265(90)4718-4721].

EXAMPLE 5

Heteroduplex Substrate Preparation for Plasmid-on-Plasmid Genetic Reassortment by DNA Mismatch Resolution (POP GRAMMR) of GFP Plasmids This example teaches that heteroduplex substrate for Genetic Reassortment by DNA Mismatch Resolution can be in the form of intact circular plasmids. Cycle 3-GFP and wild-type GFP heteroduplex molecules were prepared plasmid-on-plasmid (POP) format. In this format, the GFP sequences were reasserted within the context of a circular double-stranded plasmid vector backbone. This made possible the recovery of the reasserted product by direct transformation of E. coli using an aliquot of the GRAMMR reaction. Consequently, neither PCR amplification nor other additional manipulation of the GRAMMR-treated DNA was necessary to obtain reasserted clones.

Mismatched DNA substrate for POP-GRAMMR reactions was generated containing wild-type GFP (SEQ ID NO:01) and Cycle 3 GFP (SEQ-ID NO:02), resulting in the two pBluescript-based plasmids, pBSWTGFP (SEQ ID NO:03) and pBSC3GFP (SEQ ID NO:04), respectively. The GFPs were inserted between the KpnI and EcoRI sites of the pBluescript polylinker so that the only sequence differences between the two plasmids occurred at sites where the wild-type and Cycle 3 GFPs differ from one-another. Both plasmids were linearized by digestion of the plasmid backbone with SapI, cleaned up using a DNA spin-column, mixed, amended to IX PCR buffer (Barnes, 1994; *PNAS*, 91, 2216-2220), heated in a boiling water bath for three minutes, and slow-cooled to room temperature to anneal the denatured DNA strands. Denaturing and annealing these DNAs led to a mixture of duplexes, the re-formation of parental duplexes, and the formation of heteroduplexes from the annealing of strands from each of the two input plasmids. Parental duplexes were deemed undesirable for GRAMMR and were removed by digestion with restriction enzymes that cut in one or the other parental duplex but not in the heteroduplexed molecules. PmlI and XhoI were chosen for this operation since PmlI cuts only in the wild-type GFP sequence and XhoI cuts only Cycle 3 GFP. After treatment with these enzymes, the products were resolved on an agarose gel. The full-length, uncut heteroduplex molecules were resolved from the PmlI- and XhoI-cut parental homoduplexes in an agarose gel and purified by excision of the band and purification with a DNA spin column.

The resulting population of heteroduplexed molecules was treated with DNA ligase to convert the linear DNA into circular, double-stranded DNA heteroduplexes. After confirmation by agarose gel-shift analysis, the circular double-stranded GFP heteroduplexed plasmid was used as substrate for GRAMMR reactions. Examples of the resulting clones are included as SEQ ID NO:05, SEQ ID NO:06, SEQ ID NO:07, and SEQ ID NO:08.

EXAMPLE 6

Exemplary Reaction Parameters for Genetic Reassortment by DNA Mismatch Resolution CEL I and T4 DNA Polymerase Concentrations Compared The GRAMMR reaction involves the interaction of numerous enzymatic activities. Several parameters associated with the GRAMMR reaction were examined, such as CEL I concentration, T4 DNA polymerase concentration, reaction temperature, substitution of T4 DNA polymerase with T7 DNA polymerase, the presence of Taq DNA polymerase, and the source of the CEL I enzyme. A matrix of three different CEL I concentrations versus two concentrations of T4 DNA polymerase was set up to examine the limits of the in vitro DNA mismatch resolution reaction.

Twenty-one nanograms (21 ng) of the circular double-stranded heteroduplexed plasmid, prepared as described above, was used as substrate in a series of ten microliter reactions containing 1×NEB ligase buffer, 0.5 mM each dNTP, 1.0 unit Taq DNA polymerase, 0.2 units T4 DNA ligase (Gibco/BRL), either 1.0 or 0.2 units T4 DNA polymerase, and either 0.3, 0.1, or 0.03 microliters of a CEL I preparation (fraction 5, described in Example 1). Six reactions representing all six combinations of the two T4 DNA polymerase concentrations with the three CEL I concentrations were prepared, split into equivalent sets of five microliters, and incubated at either 20 degrees C. or 37 degrees C. A control reaction containing no CEL I and 0.2 unit of T4 DNA polymerase with the other reaction components was prepared and incubated at 37 degrees C. After 30 minutes, one microliter aliquots of each reaction were transformed into competent DH5-alpha E. coli which were then plated on LB amp plates. Colonies were picked and cultured. Plasmid DNA was extracted and examined by restriction fragment length polymorphism analysis (RFLP) followed by sequence analysis of the GFP gene sequences. RFLP analysis was based on differences in several restriction enzyme recognition sites between the wild-type and Cycle 3 GFP genes. The RFLP results showed that throughout the CEL I/T4 DNA polymerase/temperature matrix, reassortment of restriction sites, that is GRAMMR, had occurred, and that no such reassortment had occurred in the zero CEL I control clones. DNA sequence analysis confirmed that reassortment had occurred in all of the CEL I—containing samples. Sequencing also confirmed that the zero—CEL I controls were not reasserted, with the exception of a single clone of the 16 control clones, which had a single-base change from one gene sequence to the other, presumably resulting either from repair in *E. coli* or from random mutation. The sequences of several exemplary GRAMMR-reassorted GFP clones are shown; all of which came from the reaction containing 0.3 microliters of the CEL I preparation and 1.0 unit of T4 DNA polymerase incubated at 37 degrees C. The parental wild-type and Cycle 3 GFP genes are shown first for reference.

EXAMPLE 7

Taq DNA Polymerase is not Required for Genetic Reassortment by DNA Mismatch Resolution This experiment teaches that Taq DNA Polymerase does not dramatically, if at all, contribute or interfere with the functioning of Genetic Reassortment by DNA Mismatch Resolution (GRAMMR). Taq DNA polymerase is reported to have a 5' flap-ase activity, and had been included in the teachings of the previous examples as a safeguard against the possible formation and persistence of undesirable 5' flaps in the heteroduplexed DNA undergoing GRAMMR.

GRAMMR reactions were set up, as in Example 6, with twenty-one nanograms of the circular double-stranded heteroduplexed GFP plasmid substrate in ten microliter reactions containing 1×NEB ligase buffer, 0.5 mM each dNTP, 0.2 units T4 DNA ligase, 1.0 unit T4 DNA polymerase, 1.0 microliter of a CEL I preparation (fraction 5, described in Example 1), and either 2.5 units, 0.5 units of Taq DNA polymerase, or no Taq DNA polymerase. After 30 minutes, one microliter aliquots of each reaction were transformed into competent DH5-alpha *E. coli* which were then plated on LB amp plates. Colonies were picked and cultured. Plasmid DNA was extracted and examined by RFLP analysis followed by sequence analysis of the GFP gene sequences. The RFLP results showed that reassortment of restriction sites, that is, GRAMMR, had occurred both in the presence and the absence of Taq DNA polymerase in the GRAMMR reaction. DNA sequence analysis confirmed these results. Therefore, the data shows that Taq DNA polymerase was unnecessary for GRAMMR.

EXAMPLE 8

Alternate Proofreading DNA Polymerases for Genetic Reassortment by DNA Mismatch Resolution This experiment teaches that Genetic Reassortment by DNA Mismatch Resolution is not limited to the use of T4 DNA polymerase, and that alternate DNA polymerases can be substituted for it.

Reactions were set up, as in Example 6, with twenty-one nanograms of the circular double-stranded heteroduplexed GFP plasmid substrate in ten microliter reactions containing 1×NEB ligase buffer, 0.5 mM each dNTP, 0.2 units T4 DNA ligase (Gibco/BRL), 10 units or 2 units of T7 DNA polymerase, 1.0 microliter of a CEL I preparation (fraction 5, described in Example 1), and 2.5 units of Taq DNA polymerase. After 30 minutes, one microliter aliquots of each reaction were transformed into competent DH5-alpha *E. coli* which were then plated on LB amp plates. Colonies were picked and cultured. Plasmid DNA was extracted and examined by RFLP analysis followed by sequence analysis of the GFP gene sequences. The RFLP results showed that reassortment of restriction sites, that is GRAMMR, had occurred in both T7 DNA polymerase-containing reactions. DNA sequence analysis confirmed these results. Therefore, the data shows that T7 DNA polymerase can substitute for T4 DNA polymerase for GRAMMR. In addition, it shows that individual components and functionalities can be broadly substituted in GRAMMR, while still obtaining similar results.

EXAMPLE 9

Use of Cloned CEL I in the GRAMMR Reaction

This example teaches that CEL I from a cloned source can be used in place of native CEL I enzyme purified from celery in Genetic Reassortment By DNA Mismatch Resolution without any noticeable change in results.

The cDNA of CEL I was cloned from celery RNA. The gene was inserted into a TMV viral vector and expressed. Transcripts of the construct were used to infect *Nicotiana benthamiana* plants. Infected tissue was harvested, and the CEL I enzyme was purified. The GRAMMR results obtained using the purified enzyme were compared to those using CEL I purified from celery, and were found to be similar.

Reactions were set up using twenty-one nanograms of the circular double-stranded heteroduplexed GFP plasmid substrate in ten microliters containing 1×NEB ligase buffer, 0.5 mM each dNTP, 0.2 units T4 DNA ligase (Gibco/BRL), 1 unit of T4 DNA polymerase, and either 1.0 microliter of CEL I purified from celery (fraction 5, described in Example 1), or 0.3 microliters of CEL I purified from a cloned source. After 30 minutes, one microliter aliquots of each reaction were transformed into competent DH5-alpha *E. coli* which were then plated on LB amp plates. Colonies were picked and cultured. Plasmid DNA was extracted and examined by RFLP analysis followed by sequence analysis of the GFP gene sequences. The RFLP results showed that reassortment of restriction sites, that is, GRAMMR had occurred in both celery-derived CEL I, as well as cloned CEL I-containing reactions. DNA sequence analysis confirmed these results. Therefore, the data shows CEL I from a cloned source can be used in lieu of CEL I from celery for GRAMMR. In addition, the data demonstrates that it is CEL I activity that is part of the GRAMMR method, rather than a coincidental effect resulting from the purifying steps used in extracting CEL I from celery.

EXAMPLE 10

Molecular Breeding of Tobamovirus 30K Genes in a Viral Vector

In the preceding examples, Genetic Reassortment by DNA Mismatch Resolution has been taught to be useful for reasserting sequences that are highly homologous, for example, wtGFP and Cycle 3 GFP are 96% identical. The present example teaches that GRAMMR can be used to reassort more divergent nucleic acid sequences, such as genes encoding tobamovirus movement protein genes.

Heteroduplexes of two tobamovirus movement protein (MP) genes that are approximately 75% identical were generated. The heteroduplex substrate was prepared by annealing partially-complementary single-stranded DNAs of opposite strandedness synthesized by asymmetric PCR; one strand encoding the movement protein gene from the tobacco mosaic virus U1 type strain (TMV-U1) (SEQ ID NO:09), and the other strand encoding the movement protein gene from tomato mosaic virus (ToMV) (SEQ ID NO:10). The sequences of the two partially complementary movement protein genes were flanked by 33 nucleotides of absolute complementarity to promote annealing of the DNAs at their termini and to facilitate PCR amplification and cloning. The annealing reaction took place by mixing 2.5 micrograms of each single-stranded DNA in a 150 microliter reaction containing 333 mM NaCl, 33 mM MgCl12, 3.3 mM dithiothreitol, 166 mM Tris-HCl, pH 7, and incubating at 95° C. for one minute followed by slow cooling to room-temperature. GRAMMR was performed by incubating 5 microliters of the heteroduplex substrate in a 20 microliter reaction containing 1×NEB ligase buffer, 0.5 mM each dNTP, 0.4 units T4 DNA ligase (Gibco/BRL), 2.0 units of T4 DNA polymerase, and CEL I. The CEL I was from a cloned preparation and the amount that was used varied from 2 microliters of the prep, followed by five serial 3-fold dilutions. A seventh preparation with no CEL I was prepared, which served as a control.

After one hour at room-temperature, DNA was purified from the reactions using Strataprep spin DNA purification columns (Stratagene, LaJolla, Calif.) and used as templates for PCR reactions using primers designed to anneal to the flanking primer-binding sites of the two sequences. PCR products from each reaction were purified using Strataprep columns, digested with AvrII and PacI, and ligated into the movement protein slot of similarly-cut pGENEWARE-MP-Avr-Pac. This plasmid contained a full-length infectious tobamovirus-GFP clone modified with AvrII and PacI sites flanking the movement protein gene to permit its replacement by other movement protein genes. After transformation of DH5-alpha E. coli and plating, colonies were picked, cultures grown, and DNA was extracted. The movement protein inserts were subjected to DNA sequence analysis from both directions and the sequence data confirmed that in the majority of inserts derived from the GRAMMR-treated material were reasserted sequences made up of both TMV-U1 and ToMV movement protein gene sequences. The DNA sequences of several exemplary GRAMMR MP clones are shown as SEQ ID NO:11, SEQ ID NO:12, SEQ ID NO:13, SEQ ID NO:14, and SEQ ID NO:15.

EXAMPLE 11

GRAMMR Reassortment to Generate Improved Arsenate Detoxifying Bacteria

Arsenic detoxification is important for mining of arsenopyrite-containing gold ores and other uses, such as environmental remediation. Plasmid pGJ103, containing an arsenate detoxification operon (Ji and Silver, 1992)(Ji, G. and Silver, S., Regulation and expression of the arsenic resistance operon from *Staphylococcus aureus* plasmid pI258, J. Bacteriol. 174, 3684-3694 (1992), incorporated herein by reference), is obtained from Prof. Simon Silver (U. of Illinois, Chicago, Ill.). *E. coli* TG1 containing pGJ103, containing the pI258 ars operon cloned into pUC19, has a MIC (minimum inhibitory concentration) of 4 μg/ml on LB ampicillin agar plates. The ars operon is amplified by mutagenic PCR [REF], cloned into pUC19, and transformed into *E. coli* TG1. Transformed cells are plated on a range of sodium arsenate concentrations (2, 4, 8, 16 mM). Colonies from the plates with the highest arsenate levels are picked. The colonies are grown in a mixed culture with appropriate arsenate selection. Plasmid DNA is isolated from the culture. The plasmid DNA is linearized by digestion with a restriction endonuclease that cuts once into the pUC19 plasmid backbone. The linearized plasmids are denatured by heating 10 min. at 94° C. The reaction is allowed to cool to promote annealing of the single strands. Partially complementary strands that hybridize have non-basepaired nucleotides at the sites of the mismatches. Treatment with CEL I (purified by the method of Example 9) causes nicking of one or the other polynucleotide strand 3' of each mismatch. The presence of a polymerase containing a 3'-to-5' exonuclease ("proofreading") activity, such as T4 DNA polymerase allows excision of the mismatch, and subsequent 5'-to-3' polymerase activity fills in the gap using the other strand as a template. T4 DNA ligase then seals the nick by restoring the phosphate backbone of the repaired strand. The result is a randomization of mutations among input strands to give output strands with potentially improved properties. These output polynucleotides are transformed directly into *E. coli* TG1 and the cells are plated at higher arsenate levels; 8, 16, 32, 64 mM. Colonies are picked from the plates with the highest arsenate levels and another round of reassortment is performed as above except that resulting transformed cells are plated at 32, 64, 128, 256 mM arsenate. The process can then be repeated one or more times with the selected clones in an attempt to obtain additional improvements.

What is claimed is:

1. A method of obtaining a polynucleotide variant comprising the steps of:
   a) preparing at least one first heteroduplex polynucleotide from partially complementary polynucleotide strands, said first heteroduplex polynucleotide having at least two mismatched base pairs;
   b) combining said heteroduplex polynucleotide with an effective amount of purified enzymes, wherein the enzymes comprise a polymerase, a ligase and a mismatch directed endonuclease selected from the group consisting of CEL I, T4 endonuclease VII, T7 endonuclease I, and SP nuclease;
   c) allowing sufficient time for the percentage of complementarity between the strands of said heteroduplex polynucleotide to increase so that variants are made that have sequences different from any of said partially complementary polynucleotide strands;
   d) screening or selecting for a population of variants having a desired functional property from the variants;
   denaturing at least one of said population of variants to obtain single strand polynucleotides;
   f) annealing said single strand polynucleotides to form at least one second heteroduplex polynucleotide, wherein at least one strand in the second heteroduplex is a variant and said second heteroduplex polynucleotide has at least two mismatched base pairs;
   g) combining said second heteroduplex polynucleotide with an effective amount of purified enzymes, wherein the enzymes comprise a polymerase, a ligase, and a mismatch directed endonuclease selected from the group consisting of CEL I, T4 endonuclease VII, T7 endonuclease I, and SP nuclease;
   h) allowing sufficient time for the percentage of complementarity between the strands of the heteroduplex polynucleotide to increase so that additional variants are made that have sequences different from any of the partially complementary polynucleotide strands and different from any of the variants made in step c), and being different from either strand in the second heteroduplex;
   i) screening or selecting for a population of additional variants having a desired functional property from the additional variants different from any of the variants made in step c) and different from any of said partially complementary polynucleotide strands; and
   j) recovering an additional variant from the population of additional variants.

2. The method of claim 1 wherein said strands in said first or second heteroduplex polynucleotide have greater than 95% identity.

3. The method of claim 1 wherein said strands in said first heteroduplex polynucleotide are about 95%, 90%, 85%, 80% or 75% identical to each other.

4. The method of claim 1 wherein said strands in said first and second heteroduplex polynucleotides and the strands in said variants and said additional variants are full length.

5. The method of claim 1 wherein the variants and the additional variants have an improved functional property relative to either of said partially complementary polynucleotide strands.

6. The method of claim 1 wherein at least one of said additional variants has an improved functional property relative to said variants.

7. The method of claim 1 wherein the partially complementary polynucleotide strands, the first heteroduplex polynucleotide, and the second heteroduplex polynucleotide all encode a polypeptide, further comprising expressing the variants or additional variants to produce polypeptides when the variants or the additional variants encode a polypeptide and screening or selecting a polypeptide having a desired functional property.

* * * * *

SEQUENCE LISTING

```
<160> NUMBER OF SEQ ID NOS: 15

<210> SEQ ID NO 1
<211> LENGTH: 717
<212> TYPE: DNA
<213> ORGANISM: Aequorea victoria

<400> SEQUENCE: 1
atgagtaaag gagaagaact tttcactgga gttgtcccaa ttcttgttga attagatggt     60
gatgttaatg ggcacaaatt ttctgtcagt ggagagggtg aaggtgatgc aacatacgga    120
aaacttaccc ttaaatttat ttgcactact ggaaaactac ctgttccatg gccaacactt    180
gtcactactt tctcttatgg tgttcaatgc ttttcaagat acccagatca tatgaaacgg    240
catgactttt tcaagagtgc catgcccgaa ggttatgtac aggaaagaac tatatttttc    300
aaggatgacg ggaactacaa gacacgtgct gaagtcaagt ttgaaggtga tacccttgtt    360
aatagaatcg agttaaaagg tattgatttt aaagaagatg gaaacattct tggacacaaa    420
ttggaataca actataactc acacaatgta tacatcatgg cagacaaaca aaagaatgga    480
```

```
atcaaagtta acttcaaaat tagacacaac attgaagatg gaagcgttca actagcagac    540
cattatcaac aaaatactcc aattggcgat ggccctgtcc ttttaccaga caaccattac    600
ctgtccacac aatctgccct ttcgaaagat cccaacgaaa agagagacca catggtcctt    660
cttgagtttg taacagctgc tgggattaca catggcatgg atgaactata caaataa      717

<210> SEQ ID NO 2
<211> LENGTH: 717
<212> TYPE: DNA
<213> ORGANISM: Artificial Sequence
<220> FEATURE:
<223> OTHER INFORMATION: synthetic construct

<400> SEQUENCE: 2
atgagtaaag gagaagaact tttcactgga gttgtcccaa ttcttgttga attagatggt     60
gatgttaatg ggcacaaatt ttctgtcagt ggagagggtg aaggtgatgc tacatacgga    120
aagcttaccc ttaaatttat ttgcactact ggaaaactac ctgttccatg gccaacactt    180
gtcactactt tctcttatgg tgttcaatgc ttttcccgtt atccggatca tatgaaacgg    240
catgactttt tcaagagtgc catgcccgaa ggttatgtac aggaacgcac tatatctttc    300
aaagatgacg ggaactacaa gacgcgtgct gaagtcaagt ttgaaggtga taccttgtt     360 aatcgtatcg agttaaaagg tattgatttt aagaagatg gaaacattct cggacacaaa     420
ctcgagtaca actataactc acacaatgta tacatcacgg cagacaaaca aaagaatgga    480
atcaaagcta acttcaaaat cgccacaac attgaagatg gatccgttca actagcagac    540
cattatcaac aaaatactcc aattggcgat ggccctgtcc ttttaccaga caaccattac    600
ctgtcgacac aatctgccct ttcgaaagat cccaacgaaa agcgtgacca catggtcctt    660
cttgagtttg taactgctgc tgggattaca catggcatgg atgaactata caaataa      717

<210> SEQ ID NO 3
<211> LENGTH: 3637
<212> TYPE: DNA
<213> ORGANISM: Artificial Sequence
<220> FEATURE:
<223> OTHER INFORMATION: synthetic construct

<400> SEQUENCE: 3
gtggcacttt tcggggaaat gtgcgcggaa cccctatttg tttatttttc taaatacatt     60
caaatatgta tccgctcatg agacaataac cctgataaat gcttcaataa tattgaaaaa    120
ggaagagtat gagtattcaa catttccgtg tcgcccttat tcccttttttt gcggcatttt    180 gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca acatggggga tcatgtaa     600 ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
```

```
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc cttttttgata  1080 atctcatgac caaaatccct taacgtgagt tttcgttcca ctgagcgtca gaccccgtag   1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag cgcagcggt cgggctgaac ggggggttcg tgcacacagc    1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg ggcggagcc    1740 tatgaaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct gggtaccgat gagtaaagga   2220
gaagaacttt tcactggagt tgtcccaatt cttgttgaat tagatggtga tgttaatggg   2280
cacaaatttt ctgtcagtgg agagggtgaa ggtgatgcaa catacggaaa acttacccctt  2340 aaatttattt gcactactgg aaaactacct gttccatggc caacacttgt cactacttc   2400 tcttatggtg ttcaatgctt ttcaagatac ccagatcata tgaaacggca tgactttttc   2460
aagagtgcca tgcccgaagg ttatgtacag gaaagaacta tattttttcaa ggatgacggg   2520 aactacaaga cacgtgctga agtcaagttt gaaggtgata cccttgttaa tagaatcgag   2580 ttaaaggta ttgatttaa agaagatgga acattcttg gacacaaatt ggaatacaac     2640
tataactcac acaatgtata catcatggca gacaaacaaa agaatggaat caaagttaac   2700
ttcaaaatta gacacaacat tgaagatgga agcgttcaac tagcagacca ttatcaacaa   2760
aatactccaa ttggcgatgg ccctgtcctt ttaccagaca accattacct gtccacacaa   2820
tctgcccttt cgaaagatcc caacgaaaag agagaccaca tggtccttct tgagtttgta   2880
acagctgctg ggattacaca tggcatggat gaactataca ataagaatt cctgcagccc    2940 gggggatcca ctagttctag agcggccgcc accgcggtgg agctccaatt cgccctatag   3000
tgagtcgtat tacgcgcgct cactggccgt cgttttacaa cgtcgtgact gggaaaaccc   3060
tggcgttacc caacttaatc gccttgcagc acatccccct ttcgccagct ggcgtaatag   3120
cgaagaggcc cgcaccgatc gcccttccca acagttgcgc agcctgaatg gcgaatggga   3180
cgcgccctgt agcggcgcat taagcgcggc gggtgtggtg gttacgcgca gcgtgaccgc   3240
```

```
tacacttgcc agcgccctag cgcccgctcc tttcgctttc ttcccttcct ttctcgccac    3300
gttcgccggc tttccccgtc aagctctaaa tcggggctc cctttagggt tccgatttag    3360
tgctttacgg cacctcgacc ccaaaaaact tgattaggt gatggttcac gtagtgggcc    3420
atcgccctga tagacggttt ttcgcccttt gacgttggag tccacgttct ttaatagtgg    3480
actcttgttc caaactggaa caacactcaa ccctatctcg gtctattctt ttgatttata    3540
agggattttg ccgatttcgg cctattggtt aaaaaatgag ctgatttaac aaaaatttaa    3600
cgcgaatttt aacaaaatat taacgcttac aatttag                            3637

<210> SEQ ID NO 4
<211> LENGTH: 3637
<212> TYPE: DNA
<213> ORGANISM: Artificial Sequence
<220> FEATURE:
<223> OTHER INFORMATION: synthetic construct

<400> SEQUENCE: 4
gtggcacttt tcggggaaat gtgcgcggaa cccctatttg tttatttttc taaatacatt      60
caaatatgta tccgctcatg agacaataac cctgataaat gcttcaataa tattgaaaaa     120
ggaagagtat gagtattcaa catttccgtg tcgcccttat tcccttttt gcggcatttt     180 gccttcctgt ttttgctcac ccagaaacgc tggtgaaagt aaaagatgct gaagatcagt     240
tgggtgcacg agtgggttac atcgaactgg atctcaacag cggtaagatc cttgagagtt     300
ttcgccccga agaacgtttt ccaatgatga gcacttttaa agttctgcta tgtggcgcgg     360
tattatcccg tattgacgcc gggcaagagc aactcggtcg ccgcatacac tattctcaga     420
atgacttggt tgagtactca ccagtcacag aaaagcatct tacggatggc atgacagtaa     480
gagaattatg cagtgctgcc ataaccatga gtgataacac tgcggccaac ttacttctga     540
caacgatcgg aggaccgaag gagctaaccg cttttttgca caacatgggg gatcatgtaa     600
ctcgccttga tcgttgggaa ccggagctga atgaagccat accaaacgac gagcgtgaca     660
ccacgatgcc tgtagcaatg gcaacaacgt tgcgcaaact attaactggc gaactactta     720
ctctagcttc ccggcaacaa ttaatagact ggatggaggc ggataaagtt gcaggaccac     780
ttctgcgctc ggcccttccg gctggctggt ttattgctga taaatctgga gccggtgagc     840
gtgggtctcg cggtatcatt gcagcactgg ggccagatgg taagccctcc cgtatcgtag     900
ttatctacac gacggggagt caggcaacta tggatgaacg aaatagacag atcgctgaga     960
taggtgcctc actgattaag cattggtaac tgtcagacca agtttactca tatatacttt    1020
agattgattt aaaacttcat ttttaattta aaaggatcta ggtgaagatc cttttttgata    1080 atctcatgac caaaatccct taacgtgagt tttcgttcca ctgagcgtca gaccccgtag    1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
```

```
ggtttcgcca cctctgactt gagcgtcgat ttttgtgatg ctcgtcaggg gggcggagcc    1740
tatggaaaaa cgccagcaac gcggccttttt tacggttcct ggccttttgc tggccttttg    1800
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcggaaga gcgcccaata cgcaaaccgc ctctccccgc gcgttggccg attcattaat    1980
gcagctggca cgacaggttt cccgactgga agcgggcag tgagcgcaac gcaattaatg    2040
tgagttagct cactcattag gcaccccagg ctttacactt tatgcttccg gctcgtatgt    2100
tgtgtggaat tgtgagcgga taacaatttc acacaggaaa cagctatgac catgattacg    2160
ccaagcgcgc aattaaccct cactaaaggg aacaaaagct gggtaccgat gagtaaagga    2220
gaagaacttt tcactggagt tgtcccaatt cttgttgaat tagatggtga tgttaatggg    2280
cacaaatttt ctgtcagtgg agagggtgaa ggtgatgcta catacggaaa gcttaccctt    2340
aaatttattt gcactactgg aaaactacct gttccatggc caacacttgt cactactttc    2400
tcttatggtg ttcaatgctt ttcccgttat ccggatcata tgaaacggca tgacttttc    2460 aagagtgcca tgcccgaagg ttatgtacag gaacgcacta tatctttcaa agatgacggg    2520
aactacaaga cgcgtgctga agtcaagttt gaaggtgata cccttgttaa tcgtatcgag    2580 ttaaaggta ttgattttaa agaagatgga acattctcg acacaaaact cgagtacaac    2640
tataactcac acaatgtata catcacggca gacaaacaaa gaatggaat caaagctaac    2700 ttcaaaattc gccacaacat tgaagatgga tccgttcaac tagcagacca ttatcaacaa    2760
aatactccaa ttggcgatgg ccctgtcctt ttaccagaca accattacct gtcgacacaa    2820
tctgcccttt cgaaagatcc caacgaaaag cgtgaccaca tggtccttct tgagtttgta    2880
actgctgctg ggattacaca tggcatggat gaactataca ataagaatt cctgcagccc    2940 gggggatcca ctagttctag agcggccgcc accgcggtgg agctccaatt cgccctatag    3000
tgagtcgtat tacgcgcgct cactggccgt cgttttacaa cgtcgtgact gggaaaaccc    3060
tggcgttacc caacttaatc gccttgcagc acatcccccct ttcgccagct ggcgtaatag    3120
cgaagaggcc cgcaccgatc gcccttccca acagttgcgc agcctgaatg gcgaatggga    3180
cgcgccctgt agcggcgcat taagcgcggc gggtgtggtg gttacgcgca gcgtgaccgc    3240
tacacttgcc agcgccctag cgcccgctcc tttcgctttc ttcccttcct ttctcgccac    3300
gttcgccggc tttccccgtc aagctctaaa tcggggggctc cctttagggt tccgatttag    3360
tgctttacgg cacctcgacc ccaaaaaact tgattagggt gatggttcac gtagtgggcc    3420
atcgccctga tagacggttt ttcgcccttt gacgttggag tccacgttct ttaatagtgg    3480
actcttgttc caaactggaa caacactcaa ccctatctcg gtctattctt ttgatttata    3540
agggattttg ccgatttcgg cctattggtt aaaaaatgag ctgatttaac aaaaatttaa    3600
cgcgaatttt aacaaaatat taacgcttac aatttag                             3637
```

<210> SEQ ID NO 5
<211> LENGTH: 717
<212> TYPE: DNA
<213> ORGANISM: Artificial Sequence
<220> FEATURE:
<223> OTHER INFORMATION: synthetic construct

<400> SEQUENCE: 5

```
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
```

```
aaacttaccc ttaaatttat ttgcactact ggaaaactac ctgttccatg gccaacactt      180
gtcactactt tctcttatgg tgttcaatgc ttttcaagat acccagatca tatgaaacgg      240
catgactttt tcaagagtgc catgcccgaa ggttatgtac aggaacgcac tatattttc      300 aaggatgacg ggaactacaa gacacgtgct gaagtcaagt ttgaaggtga tacccttgtt      360
aatagaatcg agttaaaagg tattgatttt aaagaagatg gaaacattct tggacacaaa      420
ttggaataca actataactc acacaatgta tacatcatgg cagacaaaca aaagaatgga      480
atcaaagtta acttcaaaat tagacacaac attgaagatg gaagcgttca actagcagac      540
cattatcaac aaaatactcc aattggcgat ggccctgtcc ttttaccaga caaccattac      600
ctgtccacac aatctgccct ttcgaaagat cccaacgaaa agagagacca catggtcctt      660
cttgagtttg taacagctgc tgggattaca catggcatgg atgaactata caaataa      717

<210> SEQ ID NO 6
<211> LENGTH: 717
<212> TYPE: DNA
<213> ORGANISM: Artificial Sequence
<220> FEATURE:
<223> OTHER INFORMATION: synthetic construct

<400> SEQUENCE: 6
atgagtaaag gagaagaact tttcactgga gttgtcccaa ttcttgttga attagatggt       60
gatgttaatg ggcacaaatt ttctgtcagt ggagagggtg aaggtgatgc tacatacgga      120
aagcttaccc ttaaatttat ttgcactact ggaaaactac ctgttccatg gccaacactt      180
gtcactactt tctcttatgg tgttcaatgc ttttcaagat acccagatca tatgaaacgg      240
catgactttt tcaagagtgc catgcccgaa ggttatgtac aggaacgcac tatatctttc      300
aaagatgacg ggaactacaa gacacgtgct gaagtcaagt ttgaaggtga tacccttgtt      360
aatagaatcg agttaaaagg tattgatttt aaagaagatg gaaacattct tggacacaaa      420
ctcgagtaca actataactc acacaatgta tacatcatgg cagacaaaca aaagaatgga      480
atcaaagtta acttcaaaat tagacacaac attgaagatg gaagcgttca actagcagac      540
cattatcaac aaaatactcc aattggcgat ggccctgtcc ttttaccaga caaccattac      600
ctgtccacac aatctgccct ttcgaaagat cccaacgaaa agagagacca catggtcctt      660
cttgagtttg taacagctgc tgggattaca catggcatgg atgaactata caaataa      717

<210> SEQ ID NO 7
<211> LENGTH: 717
<212> TYPE: DNA
<213> ORGANISM: Artificial Sequence
<220> FEATURE:
<223> OTHER INFORMATION: synthetic construct

<400> SEQUENCE: 7
atgagtaaag gagaagaact tttcactgga gttgtcccaa ttcttgttga attagatggt       60
gatgttaatg ggcacaaatt ttctgtcagt ggagagggtg aaggtgatgc tacatacgga      120
aagcttaccc ttaaatttat ttgcactact ggaaaactac ctgttccatg gccaacactt      180
gtcactactt tctcttatgg tgttcaatgc ttttcccgtt atccggatca tatgaaacgg      240
catgactttt tcaagagtgc catgcccgaa ggttatgtac aggaacgcac tatatctttc      300
aaagatgacg ggaactacaa gacgcgtgct gaagtcaagt ttgaaggtga tacccttgtt      360
aatagaatcg agttaaaagg tattgatttt aaagaagatg gaaacattct cggacacaaa      420
ttggaataca actataactc acacaatgta tacatcacgg cagacaaaca aaagaatgga      480
```

```
atcaaagcta acttcaaaat tcgccacaac attgaagatg gatccgttca actagcagac    540
cattatcaac aaaatactcc aattggcgat ggccctgtcc ttttaccaga caaccattac    600
ctgtcgacac aatctgccct tcgaaagat cccaacgaaa agcgtgacca catggtcctt    660
cttgagtttg taactgctgc tgggattaca catggcatgg atgaactata caaataa      717

<210> SEQ ID NO 8
<211> LENGTH: 717
<212> TYPE: DNA
<213> ORGANISM: Artificial Sequence
<220> FEATURE:
<223> OTHER INFORMATION: synthetic construct

<400> SEQUENCE: 8
atgagtaaag gagaagaact tttcactgga gttgtcccaa ttcttgttga attagatggt     60
gatgttaatg ggcacaaatt ttctgtcagt ggagagggtg aaggtgatgc aacatacgga    120
aaacttaccc ttaaatttat ttgcactact ggaaaactac ctgttccatg gccaacactt    180
gtcactactt tctcttatgg tgttcaatgc ttttcaagat acccagatca tatgaaacgg    240
catgactttt tcaagagtgc catgcccgaa ggttatgtac aggaaagaac tatattttc     300 aaggatgacg ggaactacaa gacacgtgct gaagtcaagt ttgaaggtga tacccttgtt    360
aatagaatcg agttaaaagg tattgatttt aagaagatg gaaacattct cggacacaaa     420
ctcgagtaca actataactc acacaatgta tacatcatgg cagacaaaca aaagaatgga    480
atcaaagtta acttcaaaat tcgccacaac attgaagatg gatccgttca actagcagac    540
cattatcaac aaaatactcc aattggcgat ggccctgtcc ttttaccaga caaccattac    600
ctgtccacac aatctgccct tcgaaagat cccaacgaaa agagagacca catggtcctt    660
cttgagtttg taacagctgc tgggattaca catggcatgg atgaactata caaataa      717

<210> SEQ ID NO 9
<211> LENGTH: 795
<212> TYPE: DNA
<213> ORGANISM: Artificial Sequence
<220> FEATURE:
<223> OTHER INFORMATION: synthetic construct

<400> SEQUENCE: 9
atggctctag ttgttaaagg taaggtaaat attaatgagt ttatcgatct gtcaaagtct     60
gagaaacttc tcccgtcgat gttcacgcct gtaaagagtg ttatggtttc aaaggttgat    120
aagattatgg tccatgaaaa tgaatcattg tctgaagtaa atctcttaaa aggtgtaaaa    180
cttatagaag gtgggtatgt ttgcttagtt ggtcttgttg tgtccggtga gtggaattta    240
ccagataatt gccgtggtgg tgtgagtgtc tgcatggtta caagagaat ggaaagagcg     300 gacgaagcca cactggggtc atattacact gctgctgcta aaaagcggtt tcagtttaaa    360
gtggtcccaa attacggtat tactacaaag gatgcagaaa gaacatatg gcaggtctta     420 gtaaatatta aaatgtaaa atgagtgcg ggctactgcc ctttgtcatt agaatttgtg      480
tctgtgtgta ttgttatataa aaataatata aaattgggtt tgagggagaa agtaacgagt    540
gtgaacgatg gaggacccat ggaactttca gaagaagttg ttgatgagtt catggagaat    600
gttccaatgt cggttagact cgcaaagttt cgaaccaaat cctcaaaaag aggtccgaaa    660
aataataata atttaggtaa ggggcgttca ggcggaaggc ctaaaccaaa agtttttgat    720
gaagttgaaa aagagtttga atttttgatt gaagatgaag ccgagacgtc ggtcgcggat    780
tctgattcgt attaa                                                     795
```

<210> SEQ ID NO 10
<211> LENGTH: 807
<212> TYPE: DNA
<213> ORGANISM: Artificial Sequence
<220> FEATURE:
<223> OTHER INFORMATION: synthetic construct

<400> SEQUENCE: 10

| | | | | | |
|---|---|---|---|---|---|
| atggctctag | ttgttaaagg | aaaagtgaat | atcaatgagt | ttatcgacct | gacaaaaatg | 60 |
| gagaagatct | taccgtcgat | gtttaccect | gtaaagagtg | ttatgtgttc | caaagttgat | 120 |
| aaaataatgg | ttcatgagaa | tgagtcattg | tcagggtga | accttcttaa | aggagttaag | 180 |
| cttattgata | gtggatacgt | ctgtttagcc | ggtttggtcg | tcacgggcga | gtggaacttg | 240 |
| cctgacaatt | gcagaggagg | tgtgagcgtg | tgtctggtgg | acaaaaggat | ggaaagagcc | 300 |
| gacgaggcca | ctctcggatc | ttactacaca | gcagctgcaa | agaaaagatt | tcagttcaag | 360 |
| gtcgttccca | attatgctat | aaccacccag | gacgcgatga | aaaacgtctg | gcaagtttta | 420 |
| gttaatatta | gaaatgtgaa | gatgtcagcg | ggtttctgtc | cgctttctct | ggagtttgtg | 480 |
| tcggtgtgta | ttgtttatag | aaataatata | aaattaggtt | tgagagagaa | gattacaaac | 540 |
| gtgagagacg | gagggcccat | ggaacttaca | gaagaagtcg | ttgatgagtt | catgaagat | 600 |
| gtccctatgt | cgatcaggct | tgcaaagttt | cgatctcgaa | ccggaaaaaa | gagtgatgtc | 660 |
| cgcaaaggga | aaaatagtag | tagtgatcgg | tcagtgccga | acaagaacta | tagaaatgtt | 720 |
| aaggattttg | gaggaatgag | ttttaaaaag | aataatttaa | tcgatgatga | ttcggaggct | 780 |
| actgtcgccg | aatcggattc | gttttaa | | | | 807 |

<210> SEQ ID NO 11
<211> LENGTH: 795
<212> TYPE: DNA
<213> ORGANISM: Artificial Sequence
<220> FEATURE:
<223> OTHER INFORMATION: synthetic construct

<400> SEQUENCE: 11

| | | | | | |
|---|---|---|---|---|---|
| atggctctag | ttgttaaagg | taaggtaaat | attaatgagt | ctatcgatct | gtcaaagtct | 60 |
| gagaaacttc | tcccgtcgat | gttcacgcct | gtaaagagtg | ttatggtttc | aaaggttgat | 120 |
| aagattatgg | tccatgaaaa | tgaatcattg | tctgaagtaa | atctcttaaa | aggtgtaaaa | 180 |
| cttatagaag | gtgggtatgt | ttgcttagtt | ggtcttgttg | tgtccggtga | gtggaattta | 240 |
| ccagataatt | gccgtggtgg | tgtgagtgtc | tgcatggttg | acaagagaat | ggaaagagcg | 300 |
| gacgaagcca | cactgggtc | atattacact | gctgctgcta | aaaagcggtt | tcagttcaag | 360 |
| gtcgttccca | attatgctat | aaccacccag | gatgcagaaa | agaacatatg | gcaggtctta | 420 |
| gtaaatatta | aaaatgtaaa | aatgagtgcg | ggctactacc | ctttgtcatt | agaatttgtg | 480 |
| tctgtgtgta | ttgtttataa | aaataatata | aaattgggtt | tgagggagaa | agtaacgagt | 540 |
| gtgaacgatg | gaggacccat | ggaactttca | gaagaagttg | ttgatgagtt | catgagaat | 600 |
| gttccaatgt | cgatcaggct | tgcaaagttt | cgaaccaaat | cctcaaaaag | aggtccgaaa | 660 |
| aataataata | atttaggtaa | ggggcgttca | ggcggaaggc | ctaaaccaag | aagttttgat | 720 |
| gaagttgaaa | aagagtttga | taatttgatt | gaagatgaag | ccgagacgtc | ggtcgcggat | 780 |
| tctgattcgt | attaa | | | | | 795 |

<210> SEQ ID NO 12
<211> LENGTH: 795
<212> TYPE: DNA
<213> ORGANISM: Artificial Sequence
<220> FEATURE:
<223> OTHER INFORMATION: synthetic construct

<400> SEQUENCE: 12

| | | | | | |
|---|---|---|---|---|---|
| atggctctag | ttgttaaagg | taaggtaaat | attaatgagt | ttatcgatct | gtcaaagtct | 60 |
| gagaaacttc | tcccgtcgat | gttcacgcct | gtaaagagtg | ttatggtttc | aaaggttgat | 120 |
| aagattatgg | tccatgaaaa | tgaatcattg | tctgaagtaa | atctcttaaa | aggtgtaaaa | 180 |
| cttatagaag | gtgggtatgt | ttgcttagtt | ggtcttgttg | tgtccggtgt | gtggaattta | 240 |
| ccagataatt | gccgtggtgg | tgtgagtgtc | tgcatggttg | acaagagaat | ggaaagagcg | 300 |
| gacgaggcca | cactcggatc | ttactacact | gctgctgcta | aaaagcggtt | tcagttcaag | 360 |
| gtcgttccca | attatgctat | aaccacccag | gatgcagaaa | agaacatatg | gcaggtctta | 420 |
| gtaaatatta | aaaatgtaaa | aatgagtgcg | ggctactgcc | ctttgtcatt | agaatttgtg | 480 |
| tctgtgtgta | ttgtttataa | aaataatata | aaattgggtt | tgagggagaa | agtaacgagt | 540 |
| gtgaacgatg | gaggacccat | ggaactttca | gaagaagttg | ttgatgagtt | catggagaat | 600 |
| gttccaatgt | cggttagact | cgcaaagttt | cgaaccaaat | cctcaaaaag | aggtccgaaa | 660 |
| aataataata | atttaggtaa | ggggcgttca | ggcggaaggc | ctaaaccaaa | agttttgat | 720 |
| gaagttggaa | aagagtttga | taatttgatt | gaagatgaag | ccgagacgtc | ggtcgcggat | 780 |
| tctgattcgt | attaa | | | | | 795 |

<210> SEQ ID NO 13
<211> LENGTH: 795
<212> TYPE: DNA
<213> ORGANISM: Artificial Sequence
<220> FEATURE:
<223> OTHER INFORMATION: synthetic construct

<400> SEQUENCE: 13

| | | | | | |
|---|---|---|---|---|---|
| atggctctag | ttgttaaagg | taaggtaaat | attaatgagt | ttatcgatct | gtcaaagtct | 60 |
| gagaaacttc | tcccgtcgat | gttcacgcct | gtaaggagtg | ttatggtttc | aaaggttgat | 120 |
| aagattatgg | tccatgaaaa | tgaatcattg | tctgaagtaa | atctcttaaa | aggtgtaaaa | 180 |
| cttatagaag | gtgggtatgt | ttgcttagtt | ggtcttgttg | tgtccggtga | gtggaattta | 240 |
| ccagataatt | gccgtggtgg | tgtgagtgtc | tgcatggttg | acaagagaat | ggaaagagcg | 300 |
| gacgaagcca | cactgggtc | atattacact | gctgctgcta | aaaagcggtt | tcagtttaaa | 360 |
| gtggtcccaa | attacggtat | tactacccag | gacgcgatga | aaaacgtctg | gcaggtctta | 420 |
| gtaaatatta | aaaatgtaaa | aatgagtgcg | ggctactgcc | ctttgtcatt | agaatttgtg | 480 |
| tctgtgtgta | ttgtttataa | aaataatata | aaattgggtt | tgagggagaa | agtaacgagt | 540 |
| gtgaacgatg | gaggacccat | ggaactttca | gaagaagttg | ttgatgagtt | catggagaat | 600 |
| gttccaatgt | cgatcagact | cgcaaagttt | cgaaccaaat | cctcaaaaag | aggtccgaaa | 660 |
| aataataata | atttaggtaa | ggggcgttca | ggcggaaggc | ctaaaccaaa | agttttgat | 720 |
| gaagttgaaa | aagagtttga | taatttgatt | gaagatgaag | ccgagacgtc | ggtcgcggat | 780 |
| tctgattcgt | attaa | | | | | 795 |

```
<210> SEQ ID NO 14
<211> LENGTH: 796
<212> TYPE: DNA
<213> ORGANISM: Artificial Sequence
<220> FEATURE:
<223> OTHER INFORMATION: synthetic construct

<400> SEQUENCE: 14
atggctctag ttgttaaagg taaggtaaat attaatgagt ttatcgatct gtcaaagtct      60
gagaaacttc tcccgtcgat gttcacgcct gtaaagagtg ttatggtttc aaaggttgat     120
aagattatgg tccatgaaaa tgaatcattg tctgaagtaa atctcttaaa aggtgttaag     180
cttattgata gtggatacgt ctgtttagcc ggtttggtcg tcacgggcga gtggaattta     240
ccagataatt gccgtggtgg tgtgagtgtc tgcatggttg acaagagaat ggaaagagcg     300
gacgaagcca cactggggtc atattacact gctgctgcta aaaagcggtt tcagttcaag     360
gtcgttccca aattacggta ttactaccca ggatgcagaa agaacatat ggcaggtctt      420 agtaaatatt aaaaatgtaa aaatgagtgc gggctactgc ccgctttctc tggagtttgt     480
gtctgtgtgt attgtttata aaataatat aaaattgggt ttgagggaga agtaacgag       540 tgtgaacgat ggaggaccca tggaactttc agaagaagtt gttgatgagt tcatggagaa     600
tgttccaatg tcggttagac tcgcaaagtt tcgaaccaaa tcctcaaaaa gaggtccgaa     660
aaataataat aatttaggta aggggcgttc aggcggaagg cctaaaccaa aaagttttga     720
tgaagttgaa aaagagtttg ataatttgat tgaggatgat tcggaggcta ctgtcgccga     780
ttctgattcg tattaa                                                     796

<210> SEQ ID NO 15
<211> LENGTH: 795
<212> TYPE: DNA
<213> ORGANISM: Artificial Sequence
<220> FEATURE:
<223> OTHER INFORMATION: synthetic construct

<400> SEQUENCE: 15
atggctctag ttgttaaagg aaaagtgaat attaatgagt ttatcgatct gtcaaagtct      60
gagaaacttc tcccgtcgat gttcacgcct gtaaagagtg ttatggtttc aaaggttgat     120
aagattatgg tccatgaaaa tgaatcattg tctgaagtaa atctcttaaa aggtgtaaaa     180
cttatagaag gtgggtatgt ttgcttagtt ggtcttgttg tgtccggcga gtggaattta     240
ccagataatt gccgtggtgg tgtgagtgtc tgcatggttg acaagagaat ggaaagagcg     300
gacgaagcca cactggggtc atattacact gctgctgcaa agaaaagatt tcagttcaag     360
gtcgttccca attatgctat aaccacccag gatgcagaaa agaacatatg gcgggtctta     420
gtaaatatta aaaatgtaaa aatgagtgcg ggctactgcc cgctttctct ggagtttgtg     480
tctgtgtgta ttgtttataa aataatata aaattgggtt tgagggagaa agtaacgagt     540
gtgaacgatg aaggacccat ggaactttca gaagaagttg ttgatgagtt catggagaat     600
gttccaatgt cgatcaggct cgcaaagttt cgaaccaaat cctcaaaaag aggtccgaaa     660
aataataata atttaggtaa ggggcgttca ggcggaaggc taaaccaaa aagttttgat     720 gaagttgaaa aagagtttga taatttgatt gaagatgaag ccgagacgtc ggtcgcggat     780
tctgattcgt actaa                                                     795
```